(12) United States Patent
Shigemori et al.

(10) Patent No.: US 8,345,089 B2
(45) Date of Patent: Jan. 1, 2013

(54) RECEIVING APPARATUS AND INTRA-SUBJECT INFORMATION ACQUIRING SYSTEM

(75) Inventors: Toshiaki Shigemori, Hachioji (JP); Ayako Nagase, Hachioji (JP)

(73) Assignee: Olympus Medical Systems Corp. (JP)

( * ) Notice: Subject to any disclaimer, the term of this patent is extended or adjusted under 35 U.S.C. 154(b) by 1694 days.

(21) Appl. No.: 11/575,201

(22) PCT Filed: Sep. 8, 2006

(86) PCT No.: PCT/JP2006/317862
§ 371 (c)(1),
(2), (4) Date: Mar. 13, 2007

(87) PCT Pub. No.: WO2007/029812
PCT Pub. Date: Mar. 15, 2007

(65) Prior Publication Data
US 2009/0051762 A1 Feb. 26, 2009

(30) Foreign Application Priority Data
Sep. 9, 2005 (JP) .................. 2005-263105

(51) Int. Cl.
*A62B 1/04* (2006.01)
(52) U.S. Cl. .......................................... 348/65
(58) Field of Classification Search .......... 348/47, 348/65, 226, 540
See application file for complete search history.

(56) References Cited

U.S. PATENT DOCUMENTS

| 6,014,179 A * | 1/2000 | Kobayashi et al. ........... 348/556 |
| 6,904,308 B2 * | 6/2005 | Frisch et al. .................. 600/424 |
| 2003/0161015 A1 * | 8/2003 | Hiji ............................... 358/538 |

FOREIGN PATENT DOCUMENTS

| JP | 64-044179 | 2/1989 |
| JP | 2000-036926 | 2/2000 |
| JP | 2001231186 | 8/2001 |
| JP | 2005-159855 | 6/2005 |
| WO | WO 2007/029815 | 3/2007 |

OTHER PUBLICATIONS

Office Action issued by the Japanese Patent Office on Jun. 14, 2011 in connection With corresponding Japanese Patent Application No. 2005-263105.
Translation of the Office Action issued by the Japanese Patent Office on Jun. 14, 2011 in connection with corresponding Japanese Patent Application No. 2005-263105.
Written Opinion in PCT/JP2006/317862 dated Dec. 12, 2006.

* cited by examiner

*Primary Examiner* — Joseph Avellino
*Assistant Examiner* — Marshall McLeod
(74) *Attorney, Agent, or Firm* — Ostrolenk Faber LLP

(57) ABSTRACT

To acquire much accurate image information having no noise, without increasing load in the post-processing of the image information, a receiving apparatus 3 includes: a synchronization signal detector 34 that detects a horizontal synchronization signal and a vertical synchronization signal; an image processor 35 that performs an image generation process of each frame based on the horizontal synchronization signal and the vertical synchronization signal detected by the synchronization signal detector 34; and an image deletion controller 36a that controls to delete an image of the current frame, when a horizontal synchronization signal within one frame detected by the synchronization signal detector 34 is not continuously detected by a first predetermined number or more, or when a horizontal synchronization signal within one frame detected by the synchronization signal detector 34 is not continuously detected by a second predetermined number or more, or when a vertical synchronization signal detected by the synchronization signal detector 34 is not continuously detected by a third predetermined number or more.

16 Claims, 18 Drawing Sheets

RECEIVING APPARATUS AND INTRA-SUBJECT INFORMATION ACQUIRING SYSTEM

CROSS REFERENCE TO RELATED APPLICATION

The present application is a 35 U.S.C. §§371 national phase conversion of PCT/JP2006/317862, filed 8 Sep. 2006, which claims priority of Japanese Patent Application No.2005-263105filed 9 Sep. 2005, which is herein, incorporated by reference.

TECHNICAL FIELD

The present invention relates to a receiving apparatus and an intra-subject information acquiring system. Particularly, the present invention relates to a receiving apparatus that processes a radio signal including an information component transmitted from a transmitting apparatus, and an intra-subject information acquiring system that includes this receiving apparatus and a body-insertable apparatus.

BACKGROUND ART

In recent years, a capsule endoscope having an imaging function and a radio communication function has appeared in the field of an endoscope. This capsule endoscope has a configuration that is swallowed by a subject from the mouth to perform an observation (examination), moves within the internal organs (within the body cavity) such as the stomach and the small intestine, along a peristatic motion, and sequentially images using the imaging function, until when the capsule endoscope is naturally discharged from the body (human body).

During this observation period while the capsule endoscope is moving within the internal organs, image data acquired within the body cavity by the capsule endoscope is sequentially transmitted to the outside of the subject by the radio communication function, and is stored into a memory provided within a receiving apparatus at the outside. Because the subject carries the receiving apparatus having the radio communication function and the memory function, the subject can move freely even during the observation period after swallowing the capsule endoscope until when the capsule endoscope is discharged. After the observation, a doctor or a nurse can perform diagnosis by displaying the images of the body cavity onto a display unit such as a display, based on the image data stored in the memory of the receiving apparatus (for example, see Patent Document 1).

According to a conventional capsule endoscope, image data picked up by the capsule endoscope is radio transmitted in a data configuration similar to that of an image transfer according to an NTSC system, for example. In other words, a conventional capsule endoscope system transmits synchronization data including a vertical synchronization signal synchronized in a vertical direction and each scan line data including a horizontal synchronization data, in a state that what is called a horizontal blanking period is provided between scan line data, using image data corresponding to one image as one unit.

Patent Document 1: Japanese Patent Application Laid-open No. 2001-231186 (Page 3, FIG. 1)

DISCLOSURE OF INVENTION

Problem to be Solved by the Invention

A receiving apparatus of a conventional capsule endoscope cannot detect a vertical synchronization signal or a horizontal synchronization signal, when a radio signal transmitted from the capsule endoscope is disturbed by external noise or the like during the transmission. In this case, the receiving apparatus does not synchronize a frequency of the radio signal transmitted from the capsule endoscope with a frequency of a reference clock of the receiving apparatus. Therefore, the receiving apparatus cannot process image information from which a vertical synchronization signal cannot be detected. Similarly, when a horizontal synchronization signal cannot be detected, the receiving apparatus cannot image-process scan line data from which a horizontal synchronization signal cannot be detected, because the receiving apparatus does not synchronize a frequency of the radio signal transmitted from the capsule endoscope with a frequency of a reference clock of the receiving apparatus. Accordingly, line noise occurs when an image is displayed on a display device such as a display, resulting in a defective image. When a radio signal is disturbed by external noise or the like during a transmission, a vertical synchronization signal and a horizontal synchronization signal cannot be detected, and when an image is displayed on the display device, dot noise or the like occurs, resulting in a defective image.

According to the conventional capsule endoscope system, when only one horizontal synchronization signal cannot be taken from one image, for example, one line noise occurs in a displayed image. A workstation or the like can remove small line noise like this, by image processing image data, after the receiving apparatus acquires the image data. However, the workstation including a display device performs various kinds of image processes such as enhancement of a configuration of an image. Therefore, when an image process to remove line noise is performed, load becomes excessive, and a continuous display at a predetermined frame rate cannot be performed.

The present invention has been achieved in view of the above problems. It is an object of the present invention to provide a receiving apparatus that can acquire many pieces of accurate image information having no noise, without increasing load in the post process of image information, and an intra-subject information acquiring system that includes the receiving apparatus and a body-insertable apparatus.

Means for Solving Problem

A receiving apparatus according to one aspect of the present invention includes a detector that detects a horizontal synchronization signal from an image signal of one frame having plural line information components and the horizontal synchronization signal attached to each line information component; an image processor that performs an image generation process of each frame based on the horizontal synchronization signal detected by the detector; and a controller that controls to delete an image of a current frame, when the detector does not detect a predetermined number or more horizontal synchronization signals within one frame.

Further, the receiving apparatus may include a detector that detects a horizontal synchronization signal from an image signal of one frame having plural line information components and the horizontal synchronization signal attached to each line information component, an image processor that performs an image generation process of each frame based on the horizontal synchronization signal detected by the detector, and a controller that controls to delete an image of a current frame, when the detector does not continuously detect a predetermined number or more horizontal synchronization signals within one frame.

Further, the receiving apparatus may include a detector that detects a vertical synchronization signal from an image signal of one frame having plural line information components and the vertical synchronization signal attached to plural line information components, an image processor that performs an image generation process of each frame based on the vertical synchronization signal detected by the detector, and a controller that controls to delete an image of a current frame, when the detector does not continuously detect a predetermined number or more vertical synchronization signals.

Further, the receiving apparatus may include a detector that detects a horizontal synchronization signal and a vertical synchronization signal from an image signal of one frame having plural line information components and the horizontal synchronization signal attached to each line information component, an image processor that performs an image generation process of each frame based on the horizontal synchronization signal and the vertical synchronization signal detected by the detector, and a controller that controls to delete an image of the current frame, when the detector does not continuously detect a first predetermined number or more horizontal synchronization signals within one frame, or when the detector does not detect a second predetermined number or more horizontal synchronization signals within one frame, or when the detector does not continuously detect a third predetermined number or more vertical synchronization signals.

Further, the receiving apparatus may include a storage unit that stores an image of each frame generated by the image processor.

Further, the receiving may include a reproduction signal generator that generates a horizontal reproduction signal based on a horizontal synchronization signal detected earlier by the detector in such a manner that the horizontal reproduction signal corresponds to the horizontal synchronization signal, when the detector fails to detect the horizontal synchronization signal, and the image processor may start processing a line information component from which the detector fails to detect the horizontal synchronization signal, based on the horizontal reproduction signal.

Further, in the receiving apparatus, when the detector does not detect the horizontal synchronization signal for a predetermined period after detecting one horizontal synchronization signal, the reproduction signal generator may generate the horizontal reproduction signal.

Further, in the receiving apparatus, when the detector fails to continuously detect the horizontal synchronization signal two or more times, the controller may control to delete the image of the current frame.

Further the receiving apparatus may further include a vertical reproduction signal generator that generates a vertical reproduction signal based on a vertical synchronization signal detected earlier by the detector in such a manner that the vertical reproduction signal corresponds to the vertical synchronization signal, when the detector fails to detect the vertical synchronization signal, and the image processor may start processing a frame from which the detector fails to detect the vertical synchronization signal, based on the vertical reproduction signal.

Further, an intra-subject information acquiring system according to another aspect of the present invention includes a body-insertable apparatus that is inserted into a subject, and transmits acquired image information to the outside as a radio signal, and the reception apparatus as described above.

Further, a reception method according to still another aspect of the present invention includes the steps of: detecting a horizontal synchronization signal from an image signal of one frame having a plurality of line information components and the horizontal synchronization signal attached to each line information component; performing an image generation process of each frame based on the horizontal synchronization signal detected in the detecting step; and controlling to delete an image of a current frame, when a predetermined number or more horizontal synchronization signals are not detected within one frame in the detecting step.

Further, a reception method according to still another aspect of the present invention includes the steps of: detecting a horizontal synchronization signal from an image signal of one frame having a plurality of line information components and the horizontal synchronization signal attached to each line information component; performing an image generation process of each frame based on the horizontal synchronization signal detected in the detecting step; and controlling to delete an image of a current frame, when a predetermined number or more horizontal synchronization signals are not detected continuously within one frame in the detecting step.

Further, a reception method according to still another aspect of the present invention includes the steps of: detecting a vertical synchronization signal from an image signal of one frame having a plurality of line information components and the vertical synchronization signal attached to plural line information components; performing an image generation process of each frame based on the vertical synchronization signal detected in the detecting step; and controlling to delete an image of a current frame, when a predetermined number or more vertical synchronization signals are not detected continuously in the detecting step.

Further, a reception method according to still another aspect of the present invention includes the steps of: detecting a horizontal synchronization signal and a vertical synchronization signal from an image signal of one frame having a plurality of line information components and the horizontal synchronization signal attached to each line information component; performing an image generation process of each frame based on the horizontal synchronization signal and the vertical synchronization signal detected in the detecting step; and controlling to delete an image of a current frame, when a first predetermined number or more horizontal synchronization signals are not detected continuously within one frame in the detecting step, or when a second predetermined number or more horizontal synchronization signals are not detected continuously within one frame in the detecting step, or when a third predetermined number or more vertical synchronization signals are not detected continuously in the detecting step.

Effect of the Invention

According to the receiving apparatus of the present invention, a controller controls to delete an image of the current frame, when a horizontal synchronization signal within one frame detected by the detector is not continuously detected by a first predetermined number or more, or when a horizontal synchronization signal within one frame detected by the detector is not continuously detected by a second predetermined number or more, or when a vertical synchronization signal detected by the detector is not continuously detected by a third predetermined number or more. Therefore, only accurate image information having no noise can be acquired, and load in the post process of the image can be decreased. Further, because the image can be stored at a high compression rate, there is an effect that over-capacity of a recording unit can be prevented.

EXPLANATIONS OF LETTERS OR NUMERALS

Figure 1:
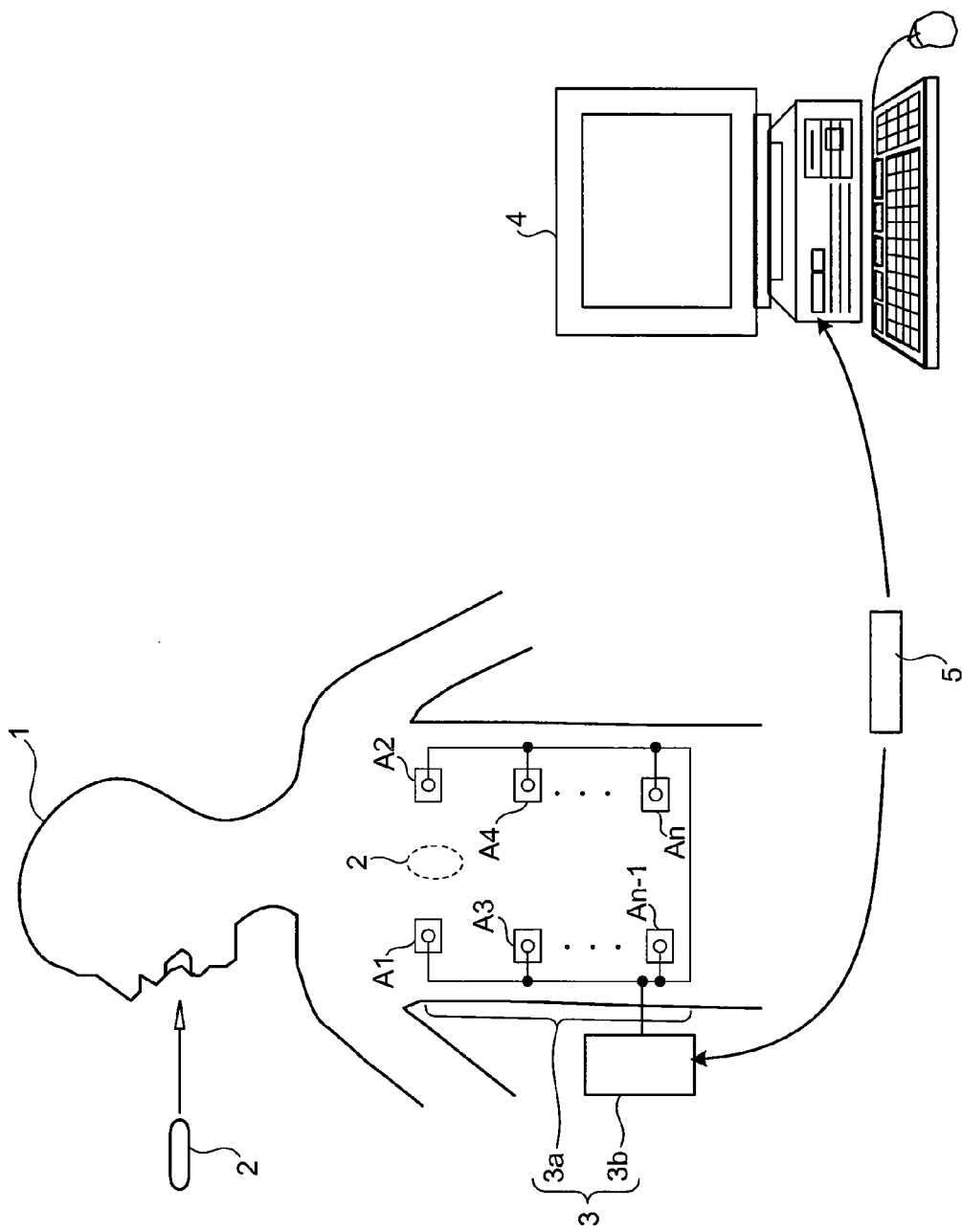
FIG. 1 is a schematic diagram showing an entire configuration of an intra-subject information acquiring system according to a first embodiment of the present invention.

1 Subject
2 Capsule endoscope
3, 203, 303, 403 Receiving apparatus
3a Antenna group
3b External device
4 Display device
5 Portable recording medium
10 Antenna board
11 Antenna element
11a opening
12 Connector
13 Wire
31 Receiving unit
33 Converter
34 Synchronization signal detector
35 Image processor
36, 336, 436, 536 Control unit
36a, 336a, 436a, 536a Image deletion controller
37 Storage unit
38 Power supply unit
39 Reference clock
236 Horizontal synchronization signal detector
237 Reproducing unit
238 Timing signal generator
239 Synchronization controller
246 Vertical synchronization signal detector
247 Reproducing unit
248 Timing signal generator

BEST MODE(S) FOR CARRYING OUT THE INVENTION

A receiving apparatus and an intra-subject information acquiring system according to best modes for carrying out the invention (hereinafter, simply "embodiment") will be explained below with reference to the accompanying drawings. Note that the drawings are schematic, and that a relationship between a thickness and a width of each part, a relationship between sizes of parts, and rates are different from real ones. It is needless to mention that the drawings include parts in which mutual size relationships and rates are different. In the description of the drawings, like parts are denoted with like reference letters or numerals. While the embodiments are explained below by examples of the application of a receiving apparatus to the intra-subject information acquiring system, it is needless to mention that the application field of the receiving apparatus according to the present invention does not need to be interpreted as being limited to the intra-subject information acquiring system.

(First Embodiment)

FIG. 1 is a schematic diagram showing an entire configuration of an intra-subject information acquiring system according to a first embodiment of the present invention. In FIG. 1, the intra-subject information acquiring system includes: a capsule endoscope 2 that is inserted into the body of a subject 1, images a body cavity, and transmits data such as an image signal to a receiving apparatus 3; and the receiving apparatus 3 having a radio receiving function. The intra-subject information acquiring system also includes; a display device 4 that displays a body-cavity image based on a radio signal received by the receiving apparatus 3; and a portable recording medium 5 that delivers data between the receiving apparatus 3 and the display device 4. The receiving apparatus 3 includes an antenna group 3a, and an external device 3b that processes a radio signal received by the antenna group 3a.

The display device 4 displays and processes a body-cavity image acquired by the capsule endoscope 2, and includes a workstation that image-displays and image-processes based on data acquired by the portable recording medium 5. The display apparatus 4 can directly display an image using a CRT display, a liquid crystal display, and the like, or can output an image to other medium such as a printer.

The portable recording medium 5 is detachable to the external device 3b and the display device 4, and can output or record information when the portable recording medium 5 is mounted on both. Specifically, while the capsule endoscope 2 is moving within the body cavity of the subject 1, the portable recording medium 5 is mounted on the external device 3b and records data transmitted from the capsule endoscope 2. After the capsule endoscope 2 is discharged from the subject 1, that is, after the capsule endoscope 2 ends imaging the inside of the subject 1, the portable recording medium 5 is taken out from the external device 3b and is mounted on the display device 4, and the recorded data is read in the display device 4. For example, when the portable recording medium 5a such as a Compact Flash (registered trademark) memory delivers data between the external device 3b and the display device 4, the subject 1 can freely move during the imaging of the body cavity, unlike when the external device 3b is connected to the display device 3b by wire. While the portable recording medium 5 is used to deliver data between the external device 3b and the display device 4, other method can be also used. For example, other built-in recording apparatus such as a hard disk can be used for the external device 3b, and the external device 3b and the display device 4 can be connected by wire or by radio to deliver data between the external device 3b and the display device 4.

The receiving apparatus 3 and the capsule endoscope 2 are explained next. In the first embodiment, the capsule endoscope 2 functions as a body-insertable apparatus in the claims, and has a function of acquiring image information as intra-subject information, and transmitting a radio signal to the receiving apparatus 3, when the capsule endoscope 2 is inserted into the subject 1.

Figure 2:
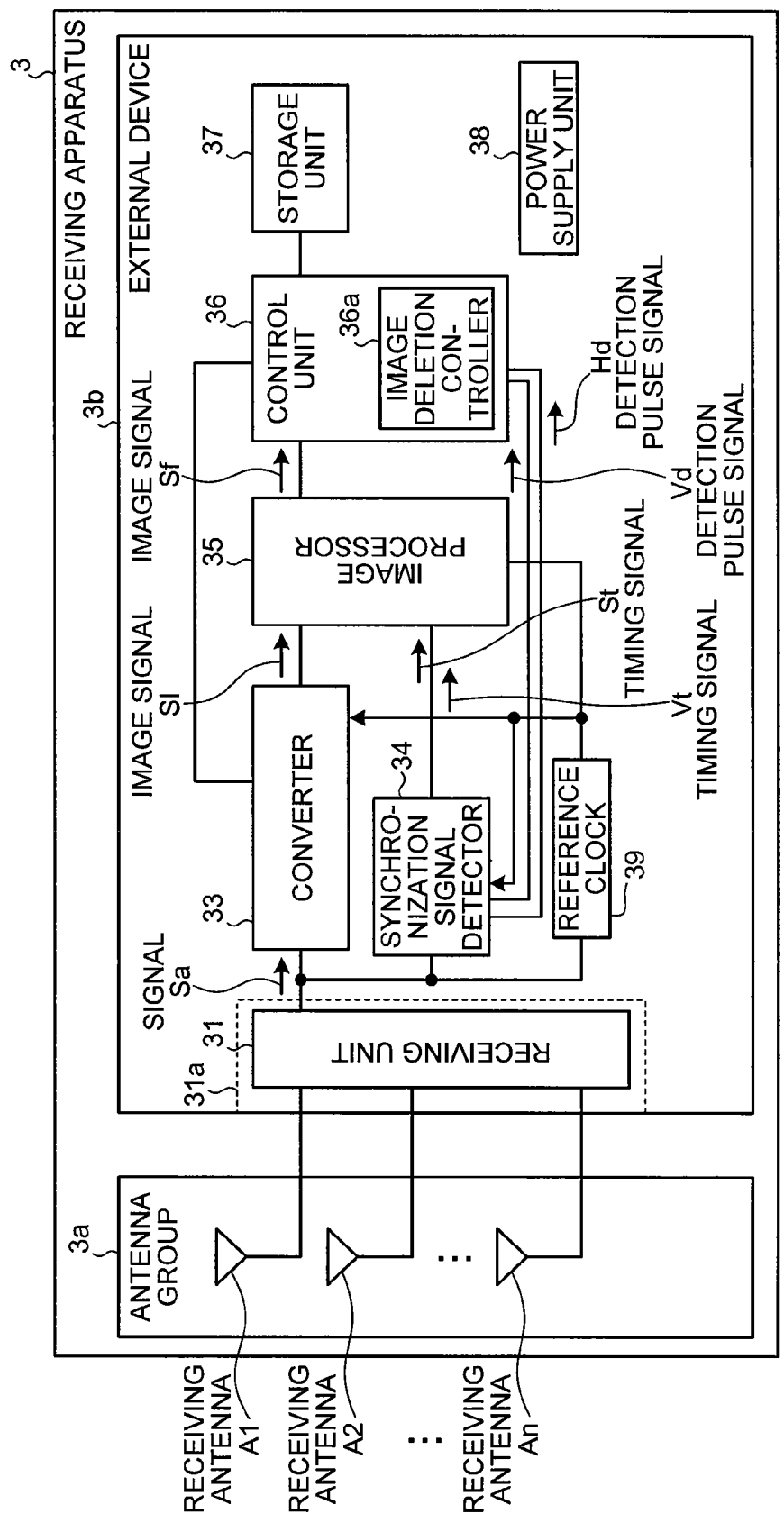
FIG. 2 is a block diagram showing a configuration of a receiving apparatus shown in FIG. 1.

The receiving apparatus 3 is explained first. FIG. 2 is a schematic block diagram showing an entire configuration of the receiving apparatus 3. As shown in FIG. 1 and FIG. 2, the receiving apparatus 3 includes the antenna group 3a having antennas A1 to An to receive radio signals transmitted from the capsule endoscope 2, and an external device 3b that performs a predetermined process to the radio signals received via the receiving antennas A1 to An.

Figure 3:
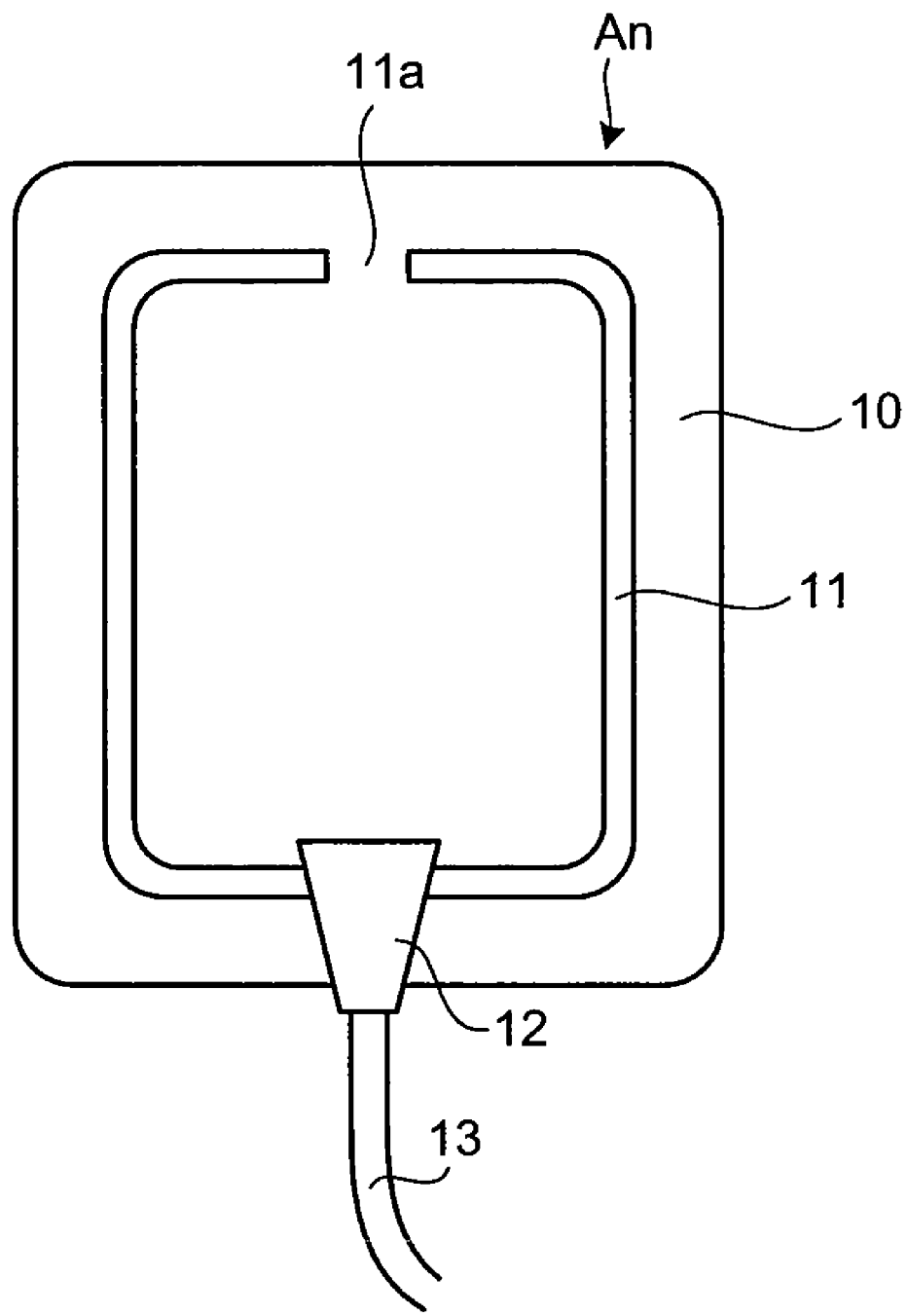
FIG. 3 shows a specific configuration example of a one receiving antenna.

The receiving antennas A1 to An receive radio signals transmitted from the capsule endoscope 2. FIG. 3 shows a specific configuration example of one receiving antenna An. The receiving antenna An has an antenna element 11 having a metal such as copper printed on the surface of a card-shaped antenna board 10 made of resin. This antenna element 11 has approximately a rectangular shape, and functions as an open loop antenna having an opening 11a formed at the opposite side of a connector 12 that connects a wire 13 as a power supply line. Each of the receiving antennas A1 to An is put into a bag made of fiber, for example, and is fixed to the subject 1 when the bag is fixed to the surface of the subject 1 with an adhesive tape or the like. In the present embodiment, the capsule endoscope 2 as a radio signal transmission source is inserted into the subject 1, and transmits a radio signal while moving within the subject 1. Therefore, a receiving antenna having the best condition of receiving a radio signal, that is, maximum reception strength, is selected from among the receiving antennas A1 to An according to a position of the capsule endoscope 2, and receives the radio signal via the selected receiving antenna, based on the control of the external device 3b.

The external device 3b performs a predetermined reception process to a radio signal received via any one of the receiving antennas A1 to An. As shown in FIG. 2, the external device 3b includes a receiving unit 31, a converter 33, a synchronization signal detector 34, an image processor 35, a control unit 36, a storage unit 37, and a power supply unit 38. The receiving unit 31 switches an antenna to be used to receive a radio signal, demodulates a radio signal received via the switched antenna, performs a reception process such as an analog/digital conversion, and outputs a demodulated digital signal Sa. In the first embodiment, the receiving unit 31 is detachable to the external device 3b as an antenna unit 31a. The converter 33 converts the signal Sa output from the receiving unit 31 into an image signal S1 in a signal format that the image processor 35 can process. For example, when the signal Sa is in a serial format, the converter 33 outputs the image signal S1 converted into a parallel format. The synchronization signal detector 34 detects various kinds of synchronization signals from the signal Sa, and outputs a timing signal St for instructing a timing of an image process performed by the image processor 35. The synchronization signal detector 34 outputs detection pulse signals Hd and Vd showing a result of a detection of various kinds of synchronization signals, to the control unit 36. The image processor 35 performs a predetermined process to the image signal S1 output from the converter 33, and outputs an image signal Sf corresponding to an image of one frame.

The control unit 36 performs the overall control within the receiving apparatus 3, and has an image deletion controller 36a. The image deletion controller 36a determines whether an image shown by the image signal Sf input from the image processor 35 is a defective image, based on detection pulse signals Hd and Vd input from the synchronization signal detector 34. When a result of this determination is that the image is a defective image, the image deletion controller 36a deletes the image without storing the image into the storage unit 37. When a result of this determination is that the image is not a defective image, the control unit 36 stores the image into the storage unit 37. A reference clock 39 outputs a clock signal that becomes a processing reference to the radio signal transmitted from the capsule endoscope 2. The storage unit 37 stores an image shown by the image signal Sf, based on the process performed by the control unit 36. The power supply unit 38 supplies driving power to each of the above constituent elements. The external device 3b detects received electric-field strength of radio signals received via the receiving antennas A1 to An. The control unit 36 selects one receiving antenna in which the received electric-field strength becomes a maximum from the plural receiving antennas, based on a result of the detection, and instructs a switch to the receiving unit 31.

Figure 4:
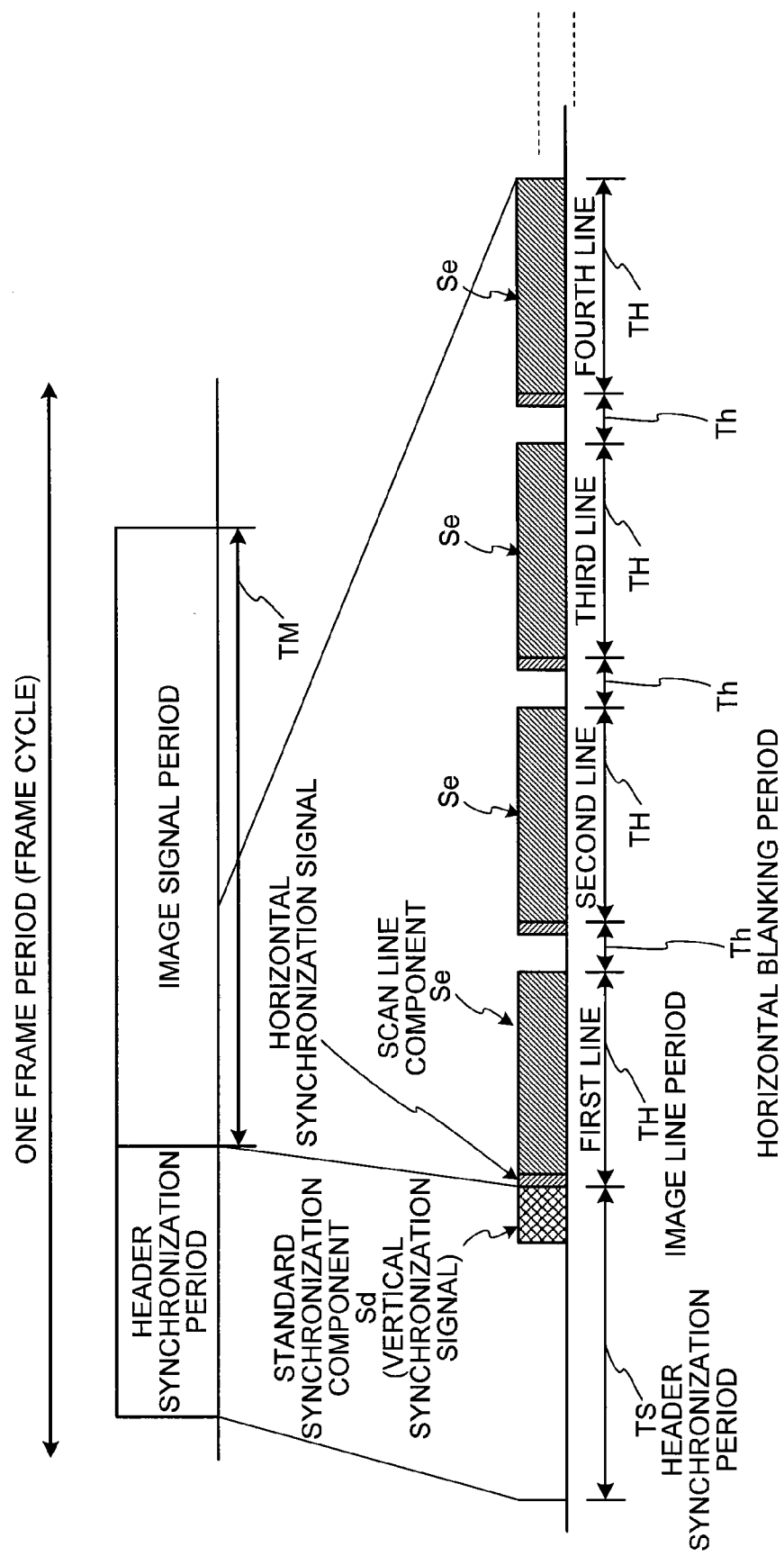
FIG. 4 is a schematic diagram showing an image signal transmitted from a capsule endoscope to a receiving apparatus.

An image signal transmitted from the capsule endoscope to the receiving apparatus 3 is explained with reference to FIG. 4. The capsule endoscope 2 outputs a scan line component Se corresponding to each scan line of image information imaged by the CCD, during an image signal period TM that constitutes one frame period (frame cycle) corresponding to one image. An image signal transmitted from the capsule endoscope 2 includes: a header synchronization period TS having a header standard synchronization component Sd including a vertical synchronization signal; and an image signal period TM during which a scan line component Se corresponding to each scan line each including a horizontal synchronization signal and a horizontal blanking period Th as a predetermined blanking period provided between the scan line components Se are alternately transmitted. The horizontal blanking period Th does not include a signal component. The vertical synchronization signal and the horizontal synchronization signal are synchronization signals that are used to reconstruct an image in the receiving apparatus 3. The vertical synchronization signal is used to synchronize in a vertical direction, and the horizontal synchronization signal is used to synchronize in a horizontal direction. The horizontal synchronization signal is attached to the header of each scan line component Se.

As described above, a transmission mode in which a reference signal for synchronizing the transmission side and the reception side is not inserted into the horizontal blanking period Th and the like is generally called an asynchronous mode. As shown in FIG. 4, in the asynchronous mode, a configuration of a signal transmitted from the capsule endoscope 2 becomes a standard synchronization component Sd in the header synchronization period TS, and becomes a scan line component Se in the image line period TH. In this case, the receiving apparatus 3 extracts a vertical synchronization signal and a horizontal synchronization signal from the received radio signal, and processes an image signal included in the received radio signal, using the vertical synchronization signal and the horizontal synchronization signal. When the capsule endoscope 2 transmits a radio signal by using the asynchronous mode, a reference signal to be inserted into the horizontal blanking period Th and the like does not need to be generated. Therefore, the capsule endoscope 2 can be made compact, and power consumption can be decreased. Particularly, the asynchronous mode is suitable for the capsule endoscope 2 to image during a long time and to transmit image information.

Figure 5:
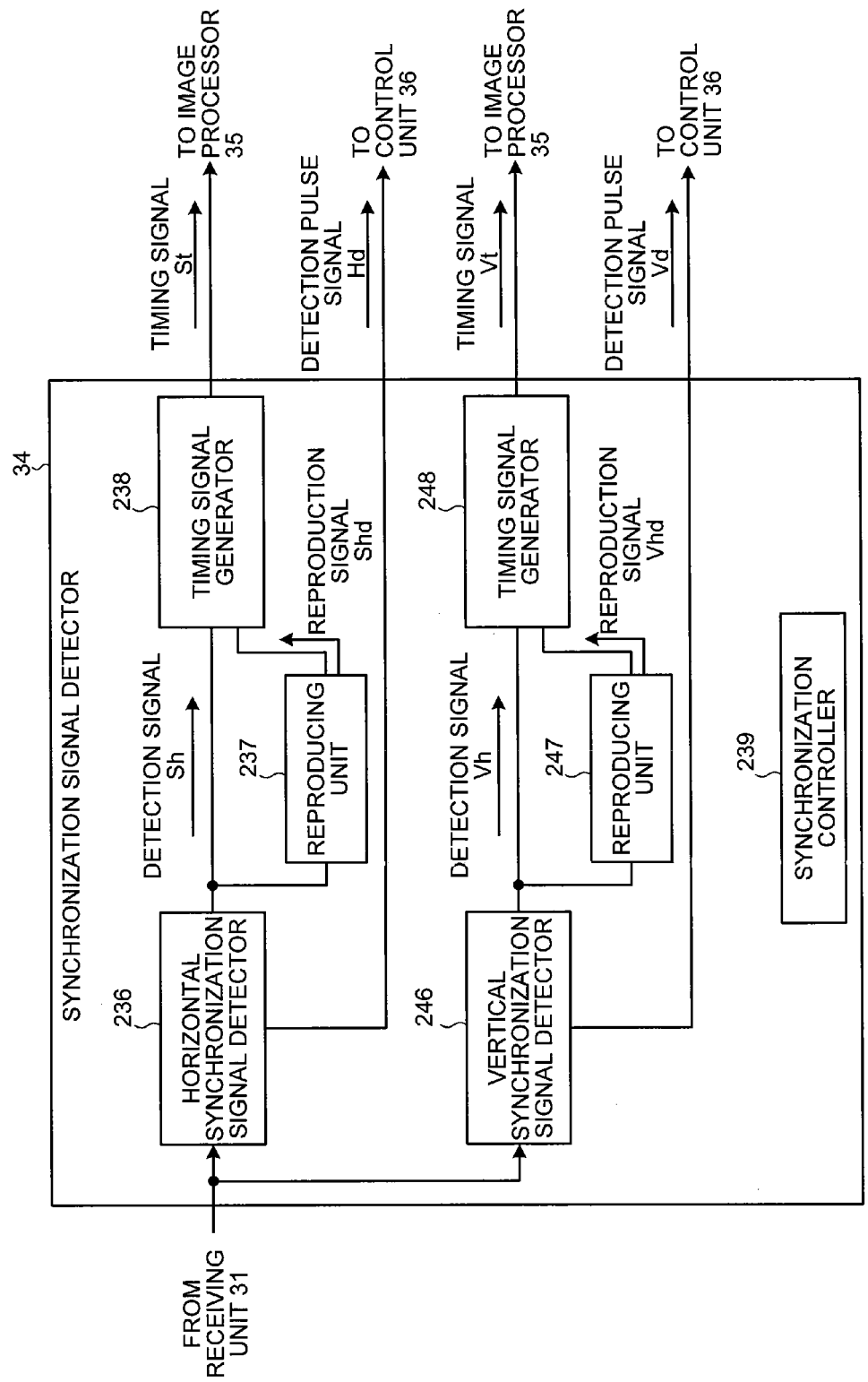
FIG. 5 is a block diagram showing an internal configuration of a synchronization signal detector of an external device shown in FIG. 2.

The synchronization signal detector 34 of the external device 3b shown in FIG. 2 is explained next. FIG. 5 is a detailed block diagram showing an internal configuration of the synchronization signal detector 34 of the external device 3b shown in FIG. 2. As shown in FIG. 5, the synchronization signal detector 34 includes a horizontal synchronization signal detector 236, a reproducing unit 237, a timing signal generator 238, a vertical synchronization signal detector 246, a reproducing unit 247, a timing signal generator 248, and a synchronization controller 239 that controls a processing operation of each constituent element of the synchronization signal detector 34.

The horizontal synchronization signal detector 236 detects a horizontal synchronization signal corresponding to each scan line from the signal Sa output from the receiving unit 31. When a horizontal synchronization signal is detected, the horizontal synchronization signal detector 236 outputs a detection signal Sh showing a detection of the horizontal synchronization signal and showing a header of a scan line component attached with this horizontal synchronization signal, to the timing signal generator 238. When a horizontal synchronization signal is detected, the horizontal synchronization signal detector 236 also outputs a detection pulse signal Hd to the control unit 36. When a predetermined part or above set in advance in a signal that forms a horizontal synchronization signal is detected from the signal Sa, the horizontal synchronization signal detector 236 outputs a detection signal Sh and a detection pulse signal Hd by assuming that a horizontal synchronization signal is detected, even when the entire signal of the horizontal synchronization signal cannot be detected.

When the horizontal synchronization signal detector 236 cannot detect a horizontal synchronization signal, the reproducing unit 237 generates a reproduction signal Shd for the scan line component, based on a horizontal synchronization signal detected last by the horizontal synchronization signal detector 236, and outputs the generated reproduction signal Shd to the timing signal generator 238. The reproducing unit 237 generates the reproduction signal Shd, when the horizontal synchronization signal detector 236 does not detect a horizontal synchronization signal during a period from when the horizontal synchronization signal detector 236 generates the last horizontal detection signal until when the horizontal synchronization signal detector 236 detects a horizontal synchronization signal for the next scan line component. This reproduction signal Shd shows a header of a scan line component from which a horizontal synchronization signal is not detected. The reproducing unit 237 generates the reproduction signal Shd, assuming that a radio signal is received from the capsule endoscope 2 following a constant image line period TH and a constant horizontal blanking period Th. Based on this assumption, the reproducing unit 237 generates and outputs the reproduction signal Shd, when the horizontal synchronization signal detector 236 does not output the detection signal Sh, after a lapse of a period from when the horizontal synchronization signal detector 236 outputs the last detection signal Sh until when the detection signal Sh is assumed to be output next.

The timing signal generator 238 outputs a timing signal St that instructs a process starting timing of a scan line component in the image signal S1, to the image processor 35, by relating the timing signal St to the input timing of a scan line component in the image signal S1 to the image processor 35, based on the detection signal Sh output from the horizontal synchronization signal detector 236 or the reproduction signal Shd output from the reproducing unit 237. The timing signal generator 238 outputs the timing signal St for each image signal constituting one pixel, out of the image signal S1. The timing signal generator 238 also advances the first output of the timing signal St based on the reproduction signal Shd, from the first output of the timing signal St based on the detection signal Sh, by a generation period of the reproduction signal generated by the reproducing unit 237. As a result, the timing signal generator 238 can accurately instruct a timing for the image processor 35 to process the image signal positioned at the head of the image signal S1, either when the detection signal Sh is used or when the reproduction signal Shd is used.

The vertical synchronization signal detector 246 detects a vertical synchronization signal corresponding to each frame out of the signal Sa output from the receiving unit 31. When a vertical synchronization signal is detected, the vertical synchronization signal detector 246 outputs a detection signal Vh showing a detection of the vertical synchronization signal and showing a header of an image signal attached with this vertical synchronization signal, to the timing signal generator 248. When a vertical synchronization signal is detected, the vertical synchronization signal detector 246 also outputs a detection pulse signal Vd to the control unit 36. When a predetermined part or above set in advance in a signal that forms a vertical synchronization signal is detected from the signal Sa, the vertical synchronization signal detector 246 outputs a detection signal Vh and a detection pulse signal Vd by assuming that a vertical synchronization signal is detected, even when the entire signal of the vertical synchronization signal cannot be detected.

When the vertical synchronization signal detector 246 cannot detect a vertical synchronization signal, the reproducing unit 247 generates a reproduction signal Vhd for the image signal, based on a vertical synchronization signal detected last by the vertical synchronization signal detector 246, and outputs the generated reproduction signal Vhd to the timing signal generator 248. The reproducing unit 247 generates the reproduction signal Vhd, when the vertical synchronization signal detector 246 does not detect a vertical synchronization signal during a period from when the vertical synchronization signal detector 246 generates the last horizontal detection signal until when the vertical synchronization signal detector 246 detects a vertical synchronization signal for the next image signal. This reproduction signal Vhd shows a header of an image signal from which a vertical synchronization signal is not detected. The reproducing unit 247 generates the reproduction signal Vhd, assuming that a radio signal is received from the capsule endoscope 2 following a constant header synchronization period TS and a constant image signal period TM. Based on this assumption, the reproducing unit 247 generates and outputs the reproduction signal Vhd, when the vertical synchronization signal detector 246 does not output the detection signal Vh, after a lapse of a period from when the vertical synchronization signal detector 246 outputs the last detection signal Vh until when the detection signal Vh is assumed to be output next.

The timing signal generator 248 outputs a timing signal Vt that instructs a process starting timing of an image signal in the image signal S1, to the image processor 35, by relating the timing signal Vt to the input timing of the image signal in the image signal S1 to the image processor 35, based on the detection signal Vh output from the vertical synchronization signal detector 246 or the reproduction signal Vhd output from the reproducing unit 247. The timing signal generator 248 outputs the timing signal Vt for each image signal S1 corresponding to one frame. Because there is a blanking period in the header synchronization period TS, the timing signal generator 248 does not advance the first output of the timing signal Vt based on the reproduction signal Vhd, from the first output of the timing signal Vt based on the detection signal Vh, by a generation period of the reproduction signal generated by the reproducing unit 247 (see FIG. 4).

Figure 6:
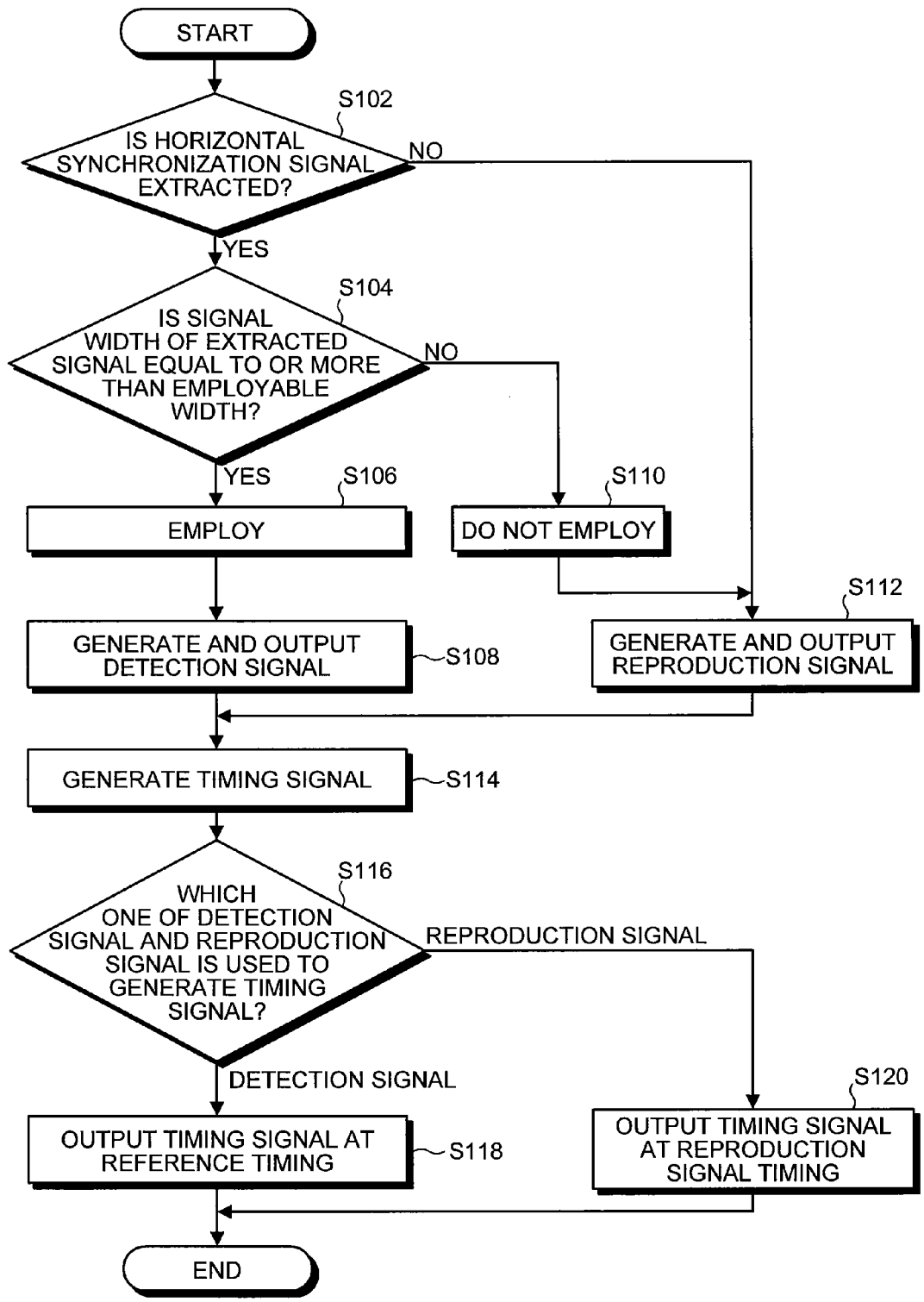
FIG. 6 is a flowchart showing a processing operation of the synchronization signal detector shown in FIG. 5.

Next, with reference to FIG. 6, the processing operation up to a stage where the synchronization signal detector 34 outputs the timing signal St based on a horizontal synchronization signal is explained next. As shown in FIG. 6, in the synchronization signal detector 34, the synchronization controller 239 first determines whether the horizontal synchronization signal detector 236 can extract a horizontal synchronization signal from the signal Sa (step S102).

When the synchronization controller 239 determines that the horizontal synchronization signal detector 236 can extract a horizontal synchronization signal (step S102: Yes), the horizontal synchronization signal detector 236 determines whether a signal width of the extracted horizontal synchronization signal is equal to or above a predetermined width, that is, whether a signal width of the extracted horizontal synchronization signal is equal to or above an employable width (step S104). When the horizontal synchronization signal detector 236 determines that a signal width of the extracted horizontal synchronization signal is equal to or above the employable width (step S104: Yes), the extracted horizontal synchronization signal is employed (step S106), the horizontal synchronization signal detector 236 generates a detection signal Sh, and outputs the signal to the timing signal generator 238 (step S108). On the other hand, when the horizontal synchronization signal detector 236 determines that a signal width of the extracted horizontal synchronization signal is not equal to or above the employable width (step S104: No), the horizontal synchronization signal detector 236 does not employ this horizontal synchronization signal (step S110), and the process proceeds to step S112. In this case, the horizontal synchronization signal detector 236 does not generate or output the detection signal Sh.

When the synchronization controller 239 determines that the horizontal synchronization signal detector 236 cannot extract a horizontal synchronization signal (step S102: No), or when the horizontal synchronization signal detector 236 does not employ the extracted horizontal synchronization signal (step S110) and does not generate the detection signal Sh, the synchronization controller 239 instructs the reproducing unit 237 to generate the reproduction signal Shd. The reproducing unit 237 generates the reproduction signal Shd, and outputs this signal to the timing signal generator 238 (step S112).

The timing signal generator 238 generates a timing signal St, using the received detection signal Sh or the reproduction signal Shd (step S114). The synchronization controller 239 determines whether the timing signal generator 238 generates the timing signal St using either the detection signal Sh or the reproduction signal Shd (step S116).

When the synchronization controller 239 determines that the timing signal generator 238 generates the timing signal St using the detection signal Sh (step S116: the detection signal), the synchronization controller 239 makes the timing signal generator 238 output the timing signal St at a predetermined reference timing (step S118). This reference timing does not take into account a generation period during which the reproducing unit 237 generates the reproduction signal Shd. The timing signal generator 238 outputs the timing signal St after a lapse of a predetermined reference waiting period since the detection signal Sh is input from the horizontal synchronization signal detector 236, following the reference timing, and, thereafter, outputs the timing signal St at a constant timing.

On the other hand, when the synchronization controller 239 determines that the timing signal generator 238 generates the timing signal St using the reproduction signal Shd (step S116: the reproduction signal), the synchronization controller 239 makes the timing signal generator 238 output the timing signal St at a reproduction signal timing. This reproduction signal timing takes into account a generation period during which the reproducing unit 237 generates the reproduction signal. The timing signal generator 238 outputs the timing signal St after a lapse of a predetermined reproduction waiting period since the reproduction signal Shd is input from the reproducing unit 238, following the reference signal timing, and, thereafter, outputs the timing signal St at a constant output timing (step S120). The reproduction waiting period is the period from when the reproduction signal Shd is input until when the timing signal St generated based on the reproduction signal Shd is output, subtracted by the period during which the reproducing unit 237 generates the reproduction signal, as compared with the period from when the detection signal Sh is input until when the timing signal St generated based on the detection signal Sh is output. As explained above, the timing signal output unit 238 outputs the timing signal St by changing the output timing, by relating the output timing to either the detection signal Sh or the reproduction signal Shd. The processing operation up to a stage where the synchronization signal detector 34 outputs the timing signal Vt based on a vertical synchronization signal is substantially the same as the process from step S102 to step S114 shown in FIG. 6.

Figure 7:
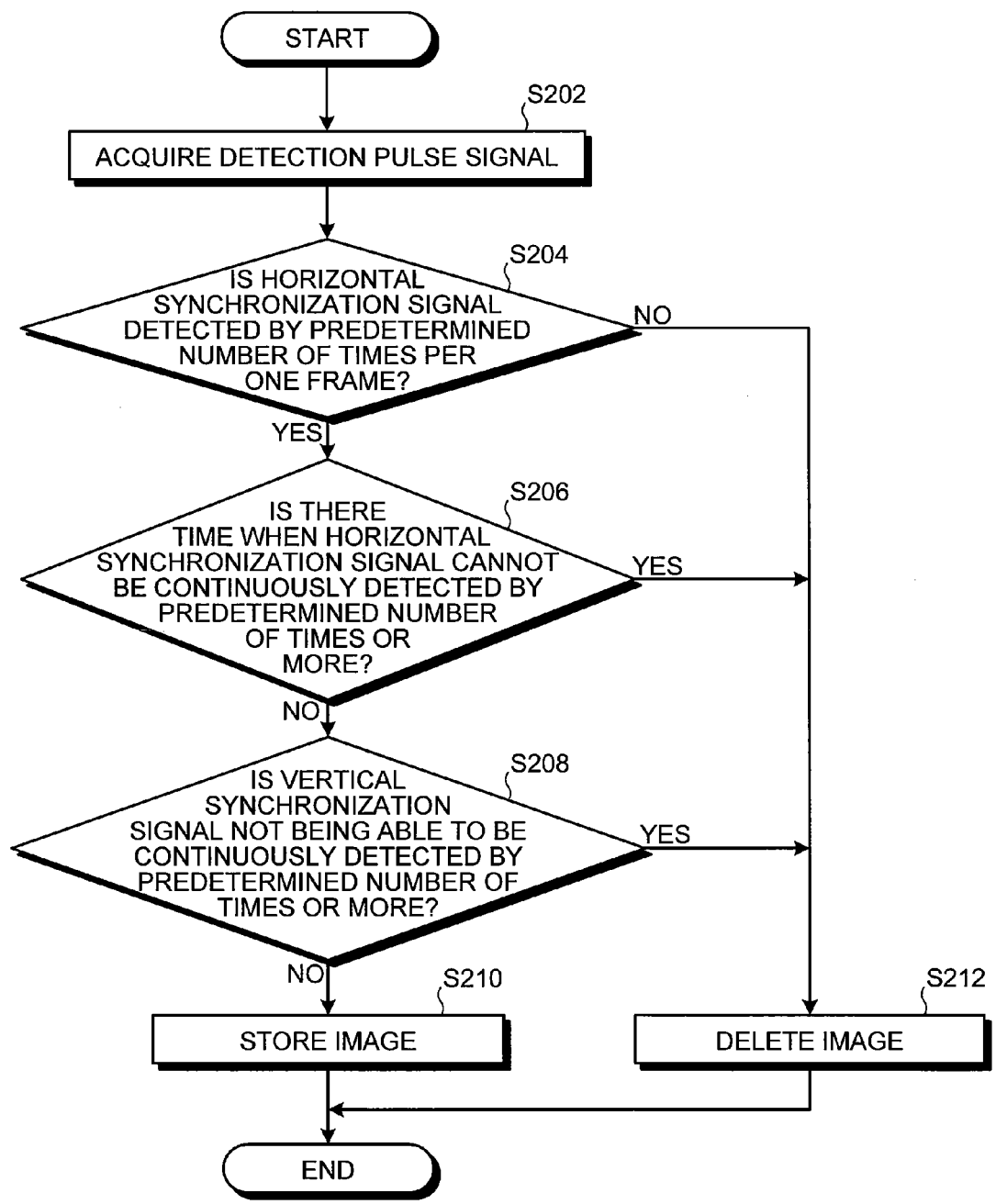
FIG. 7 is a flowchart showing a process procedure of image deletion control performed by an image deletion controller according to the first embodiment of the present invention.

A process procedure of the image deletion control performed by the image deletion controller 36a of the control unit 36 is explained with reference to FIG. 7. First, the image deletion controller 36a acquires a detection pulse signal Hd of a horizontal synchronization signal input from the horizontal synchronization signal detector 236, and a detection pulse signal Vd of a vertical synchronization signal input from the vertical synchronization signal detector 246 (step S202). When the horizontal synchronization signal detector 236 extracts a horizontal synchronization signal, the detection pulse signal Hd is output from the horizontal synchronization signal detector 236. When the vertical synchronization signal detector 246 extracts a vertical synchronization signal, the detection pulse signal Vd is output from the vertical synchronization signal detector 246.

The image deletion controller 36a determines whether the horizontal synchronization signal detector 236 detects a horizontal synchronization signal by a predetermined number or more per one frame, based on the detection pulse signal Hd (step S204). When the horizontal synchronization signal detector 236 does not detect a horizontal synchronization signal by a predetermined number or more per one frame (step S204: No), the image deletion controller 36a deletes the image of this frame as a defective image (step S212). This is because, when many horizontal synchronization signals cannot be detected, there is a high possibility that this frame is disturbed by external noise. When an image that contains much external noise is compressed to the JPEG or the like, a compression rate cannot be increased because resolution of the external noise is high. When there are 294 horizontal synchronization signals (294 lines) per one frame, for example, a threshold value is set to 260. When less than 260 horizontal synchronization signals are detected, the image deletion controller 36a determines that the image is a defective image.

On the other hand, when the horizontal synchronization signal detector 236 detects a horizontal synchronization signal by a predetermined number or more per one frame (step S204: Yes), the image deletion controller 36a further determines whether the horizontal synchronization signal detector 236 has not been able to continuously detect a horizontal synchronization signal by a predetermined number of times or more in one frame, based on the detection pulse signal Hd of a horizontal synchronization signal (step S206). When the image deletion controller 36a determines that the horizontal synchronization signal detector 236 has not been able to continuously detect a horizontal synchronization signal by a predetermined number of times or more (step S206: Yes), the image deletion controller 36a deletes the image of this frame as a defective image (step S212).

This image deletion control is performed for the following reason. When the horizontal synchronization signal detector 236 cannot detect a horizontal synchronization signal, the reproduction signal Shd is generated, and the processing of the image signal S1 is started based on the reproduction signal Shd. When the horizontal synchronization signal detector 236 cannot continuously detect a horizontal synchronization signal by a predetermined number of times or more, a possibility that a normal image can be reproduced based on the reproduction signal Shd becomes low. This is because asynchronous mode is employed as a transmission mode in the first embodiment, a phase difference occurs between the synchronization at the capsule endoscope 2 side and the synchronization at the receiving apparatus 3 side. For example, when a driving clock frequency at the capsule endoscope 2 side is 27 MHz and when a driving clock frequency at the receiving apparatus 3 side is 27 MHz, a phase difference becomes a maximum 45 ppm. When this value is converted to a threshold value at which a normal image can be reproduced, the threshold value becomes about 1.8 lines. As a result, when the driving clock frequency at the capsule endoscope 2 side and at the receiving apparatus 3 side is set to 27 MHz, respectively, when a horizontal synchronization signal cannot be continuously detected by two or more times, it is preferable to control to delete the image of this one frame.

On the other hand, when the image deletion controller 36a determines that there is no time when the horizontal synchronization signal detector 236 cannot continuously detect a horizontal synchronization signal by a predetermined number of times or more (step S206: No), the image deletion controller 36a further determines whether the vertical synchronization signal detector 246 cannot continuously detect a vertical synchronization signal by a predetermined number of times or more, based on the detection pulse signal Vd of the vertical synchronization signal (step S208). When it is determined that the vertical synchronization signal detector 246 cannot continuously detect a vertical synchronization signal by a predetermined number of times or more (step S208: Yes), the image deletion controller 36a deletes the image of this frame as a defective image (step S212).

This image deletion control is performed for the following reason. When the vertical synchronization signal detector 246 cannot detect a vertical synchronization signal, the reproduction signal Vhd is generated, and the processing of the image signal S1 is started based on the reproduction signal Vhd. When the vertical synchronization signal detector 246 cannot continuously detect a vertical synchronization signal by a predetermined number of times or more, a possibility that a normal image can be reproduced based on the reproduction signal Vhd becomes low. This is because asynchronous mode is employed as a transmission mode in the first embodiment, like in the horizontal synchronization signal, a phase difference occurs between the synchronization at the capsule endoscope 2 side and the synchronization at the receiving apparatus 3 side. For example, when vertical synchronization signals cannot be continuously detected up to 18 signals, a phase difference can be permitted using a mask or the like on the display screen. However, when 19 or more vertical synchronization signals cannot be detected continuously, a phase difference exceeds a permissible range, and a phenomenon of a color reversal occurs in some cases. In this case, when 19 or more vertical synchronization signals cannot be detected continuously, it is preferable to delete the image of one frame.

Thereafter, when it is determined that the vertical synchronization signal detector 246 cannot continuously detect a vertical synchronization signal by a predetermined number of times or more (step S208: No), the image deletion controller 36a controls to store the image of this frame into the storage unit 37 (step S210). In other words, when it is determined that the horizontal synchronization signal detector 236 can detect a horizontal synchronization signal by a predetermined number or more per one frame (step S204: Yes), and when it is determined that there is no time when the horizontal synchronization signal detector 236 cannot continuously detect a horizontal synchronization signal by a predetermined number of times or more (step S206: No), and also when it is determined that the vertical synchronization signal detector 246 cannot continuously detect a vertical synchronization signal by a predetermined number of times or more (step S208: No), the image deletion controller 36a controls to store the image of this frame into the storage unit 37 (step S210), and ends this process.

Figure 8:
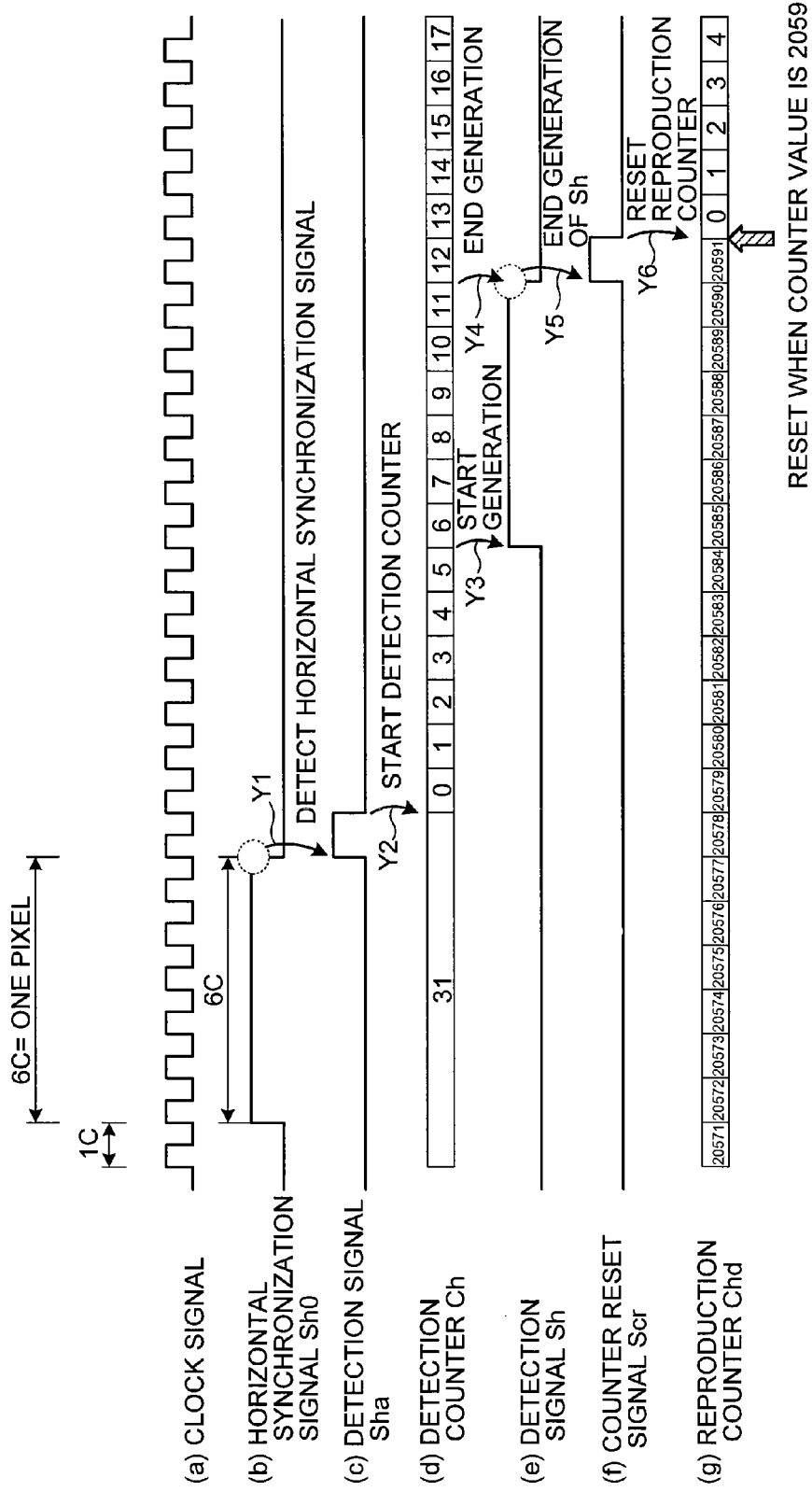
FIG. 8 is a timing chart for explaining a detection signal generation and output process shown in FIG. 6.

Each process explained in FIG. 6 is explained in detail below with reference to a timing flowchart shown in FIG. 8 and onward. First, a signal processing up to a stage where the horizontal synchronization signal detector 236 outputs the detection signal Sh is explained. FIG. 8 shows a timing chart of each signal and each counter from when the horizontal synchronization signal detector 236 detects a horizontal synchronization signal until when the detection signal Sh is output. In FIG. 8, (a) corresponds to a clock signal that is input from the reference clock 39 to the synchronization controller 239. A signal (6C) of six blocks corresponds to a signal width of a pixel signal per one pixel. A symbol (b) corresponds to a horizontal synchronization signal Sh0 that is extracted by the horizontal synchronization signal detector 236. A symbol (c) corresponds to a detection signal Sha that is output to the synchronization controller 239 when the horizontal synchronization signal detector 236 detects the horizontal synchronization signal Sh0. A symbol (d) corresponds to a count value of a detection counter Ch for a detection signal generation that the synchronization controller 239 has. A symbol (e) corresponds to a detection signal Sh that is generated by the horizontal synchronization signal detector 236. A symbol (f) corresponds to a counter reset signal Scr to a reproduction counter Chd that the synchronization controller 239 has. A symbol (g) corresponds to a count value of the reproduction counter Chd.

In FIG. 8, as shown in (b), when the horizontal synchronization signal detector 236 extracts the horizontal synchronization signal Sh0 corresponding to 6C (it is explained that the entire signal width of the horizontal synchronization signal Sh0 corresponds to the width of 6C), for example, the horizontal synchronization signal detector 236 detects a fall portion of the horizontal synchronization signal Sh0, as shown by an arrowhead Y1. The horizontal synchronization signal detector 236 outputs the detection signal Sha at the next fall portion of the horizontal synchronization signal Sh0. As shown in (b), upon receiving the detection signal Sha, the synchronization controller 239 resets the count value of the detection counter Ch to "0", as shown by an arrowhead Y2, and starts counting following the clock signal. The horizontal synchronization signal detector 236 starts generation and output of the detection signal Sh when the count value of the detection counter Ch is "6", as shown by an arrowhead Y3, based on the control of the synchronization controller 239, and stops the generation and output of the detection signal Sh when the count value is "11", as shown by an arrowhead Y4. In other words, the horizontal synchronization signal detector 236 generates and outputs the detection signal Sh of 6C corresponding to one pixel, since detecting the fall portion of the horizontal synchronization signal. Thereafter, the horizontal synchronization signal detector 236 outputs the counter reset signal Scr to the synchronization controller 239, after generating the detection signal Sh, that is, when the count value of the detection counter Ch is "12", as shown by an arrow head Y5. The synchronization controller 239 receives the counter reset signal Scr, returns a count value "20591" counted by the reproduction counter Chd to "0", and starts counting following the clock signal, as shown by an arrowhead Y6. A width from the count value "0" to the count value "20591" corresponds to an image signal width of one scan line including the horizontal synchronization signal. Therefore, when the output of the detection signal Sh ends, the synchronization controller 239 determines that the detection of the horizontal synchronization signal in the scan line has ended normally, and resets the count value of the reproduction counter Chd. The synchronization controller 239 starts again the counting of the reproduction counter Chd, to determine whether a horizontal synchronization signal in the next scan line can be detected.

Next, a signal processing from generation to output of the reproduction signal Shd by the reproducing unit 237 is explained with reference to a timing chart shown in FIG. 9. Timing charts (a) to (f) in FIG. 9 correspond to the clock signal, the horizontal synchronization signal Sh0, the detection signal Sha, the count value of the detection counter Ch, the detection signal Sh, and the count value of the reproduction counter Chd, respectively. A symbol (g) in FIG. 9 corresponds to a reproduction signal Shd generated by the reproducing unit 237, and (h) corresponds to the counter reset signal Scr explained in FIG. 9.

In FIG. 9(b), when the horizontal synchronization signal detector 236 does not detect the horizontal synchronization signal Sh0 as shown by an arrowhead Y7, the detection signal Sha is not generated, and the count value of the detection counter Ch is not reset, as shown by (c) and an arrowhead Y8. As a result, the detection signal Sh is not output from the horizontal synchronization signal detector 236, as shown by (e) and an arrowhead Y9. In this case, in FIG. 9(e), the synchronization controller 239 determines that the horizontal synchronization signal detector 236 does not detect a horizontal synchronization signal, when it is determined that there is no instruction to the reproduction counter Chd to reset the count value and start counting based on the count reset signal Scr, even when the count value of the reproduction counter Chd is "20591", as shown by an arrowhead Y11. The synchronization controller 239 instructs the reproducing unit 237 to generate the reproduction signal Shd. The count value "20591" of the reproduction counter Chd corresponds to a lapse of a period corresponding to an image signal width of one scan line. When the count value is "20591", when the horizontal synchronization signal Sh0 is normally detected, the generation and output of the detection signal Sh are completed, and the output of the counter reset signal Scr is completed, as shown in FIG. 8. Therefore, when the counter reset signal Scr is not received when the count value of the reproduction counter Chd is "20591", the synchronization controller 239 determines that the horizontal synchronization signal detector 236 cannot detect the horizontal synchronization signal Sh0, and the detection signal Sh is not output, during this period.

In this case, the reproducing unit 237 starts generation and output of the reproduction signal Shd when the count value is "20597" after 6C including the count value "20591" of the reproduction counter Chd, as shown by an arrowhead Y12, and stops generation and output of the reproduction signal when the count value is "20602", as shown by an arrowhead Y13, based on the control of the synchronization controller 239. The reproducing unit 267 outputs the counter reset signal Scr to the synchronization controller 239, after ending the generation of the reproduction signal Shd, as shown by an arrowhead Y14. The synchronization controller 239 receives this counter reset signal, and resets the count value of the reproduction counter Chd to "0", thereby making the reproduction counter Chd start counting, as shown by an arrowhead Y15.

Figure 9:
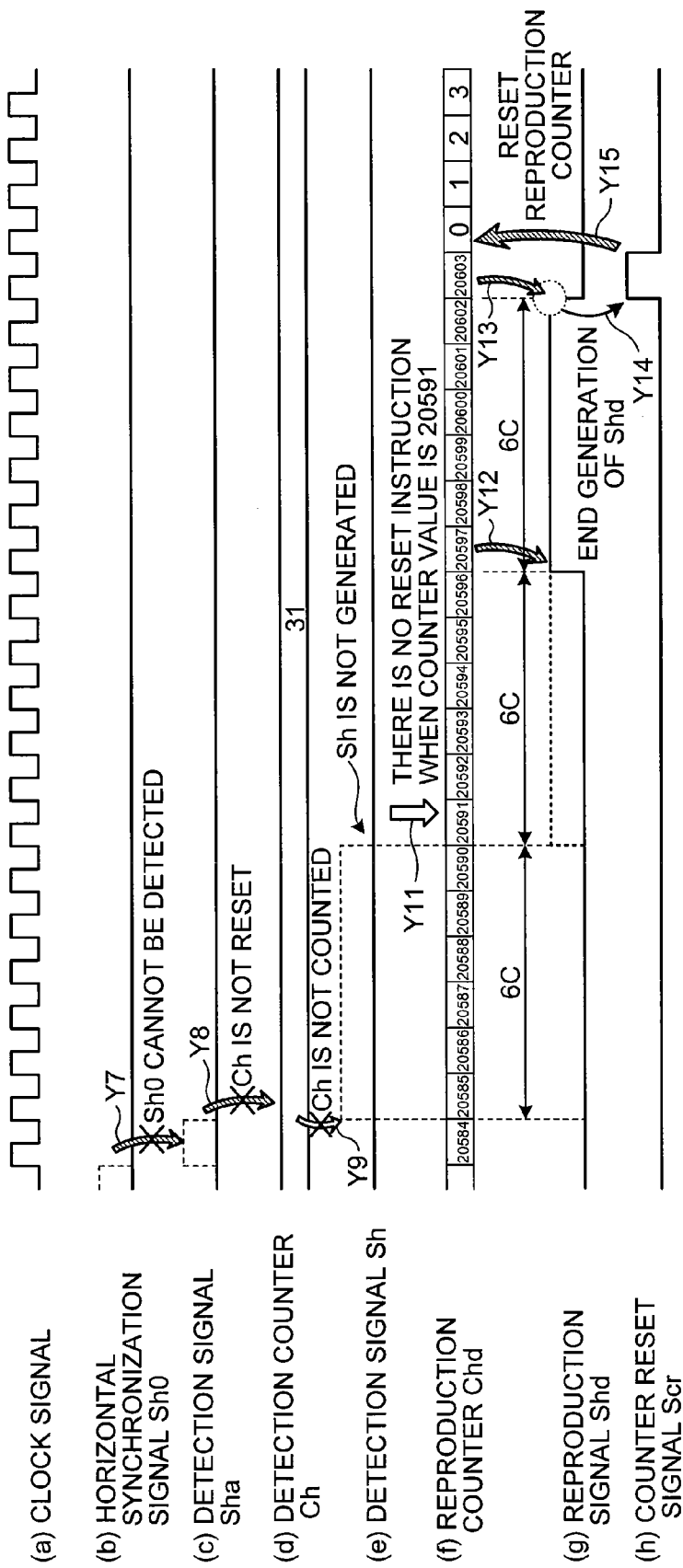
FIG. 9 is a timing chart for explaining the detection signal generation and output process shown in FIG. 6.

As shown in FIG. 9, the reproducing unit 237 generates and outputs the reproduction signal Shd at a late timing after 12C width, that is, after a signal width of two pixels, from the output timing of the detection signal Sh output from the horizontal synchronization signal detector 236.

Figure 10:
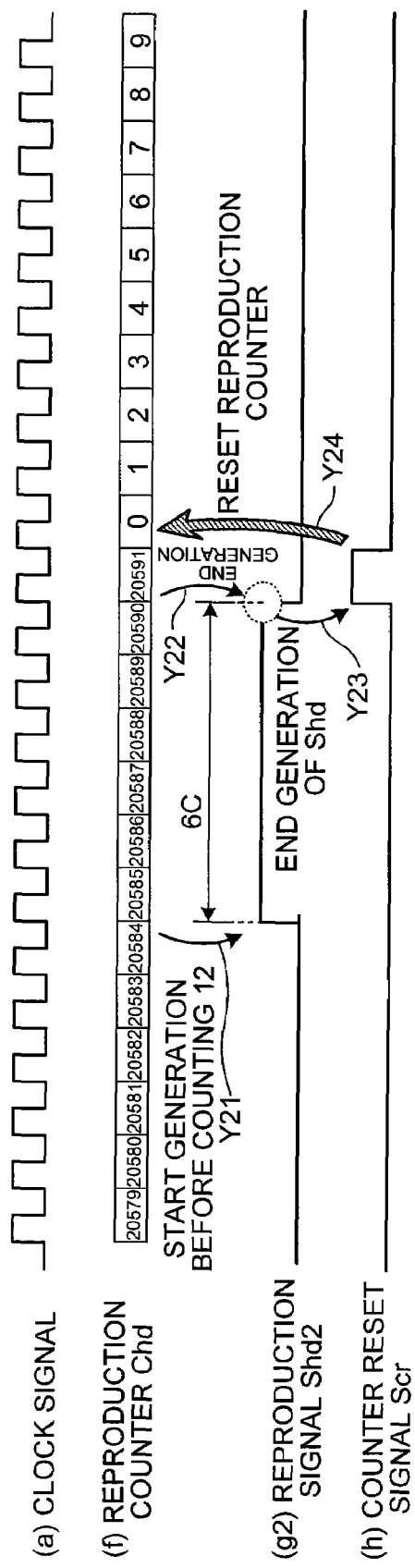
FIG. 10 is a timing chart for explaining the detection signal generation and output process shown in FIG. 6.

The generation and output of the reproduction timing Shd at this late timing need to be absorbed. Therefore, in order to generate and output a reproduction timing Shd2 for the scan line component next to the scan line component for which the reproduction signal Shd is generated and output, the reproducing unit 237 generates and outputs the reproduction signal at a timing earlier by the period corresponding to the signal width of two pixels. Specifically, as shown by an arrowhead Y21 in FIG. 10 (f)(g2), the reproducing unit 237 starts generation and output of the reproduction signal Shd2 when the count value is "20584" which is 12C earlier than the generation timing of the first-generated reproduction signal Shd, by relating this timing to a scan line next to the scan line for which the reproduction signal Shd is generated and output. In this way, the reproducing unit 237 generates the reproduction signal Shd2 at a timing earlier by 12C width, that is, a period corresponding to the signal width of two pixels. The reproducing unit 237 stops generation and output of the reproduction signal Shd2 when the count value is "20590" after 6C width from the count vale "20584", as shown by an arrowhead Y22. Thereafter, as shown by an arrowhead Y23, the counter reset signal Scr is output to the synchronization controller 239 after ending the generation of the reproduction signal Shd2. The synchronization controller 239 receives the counter reset signal Scr, and resets the count value of the reproduction counter Chd to "0", thereby making the reproduction counter Chd start counting, as shown by an arrowhead Y24.

Figure 11:
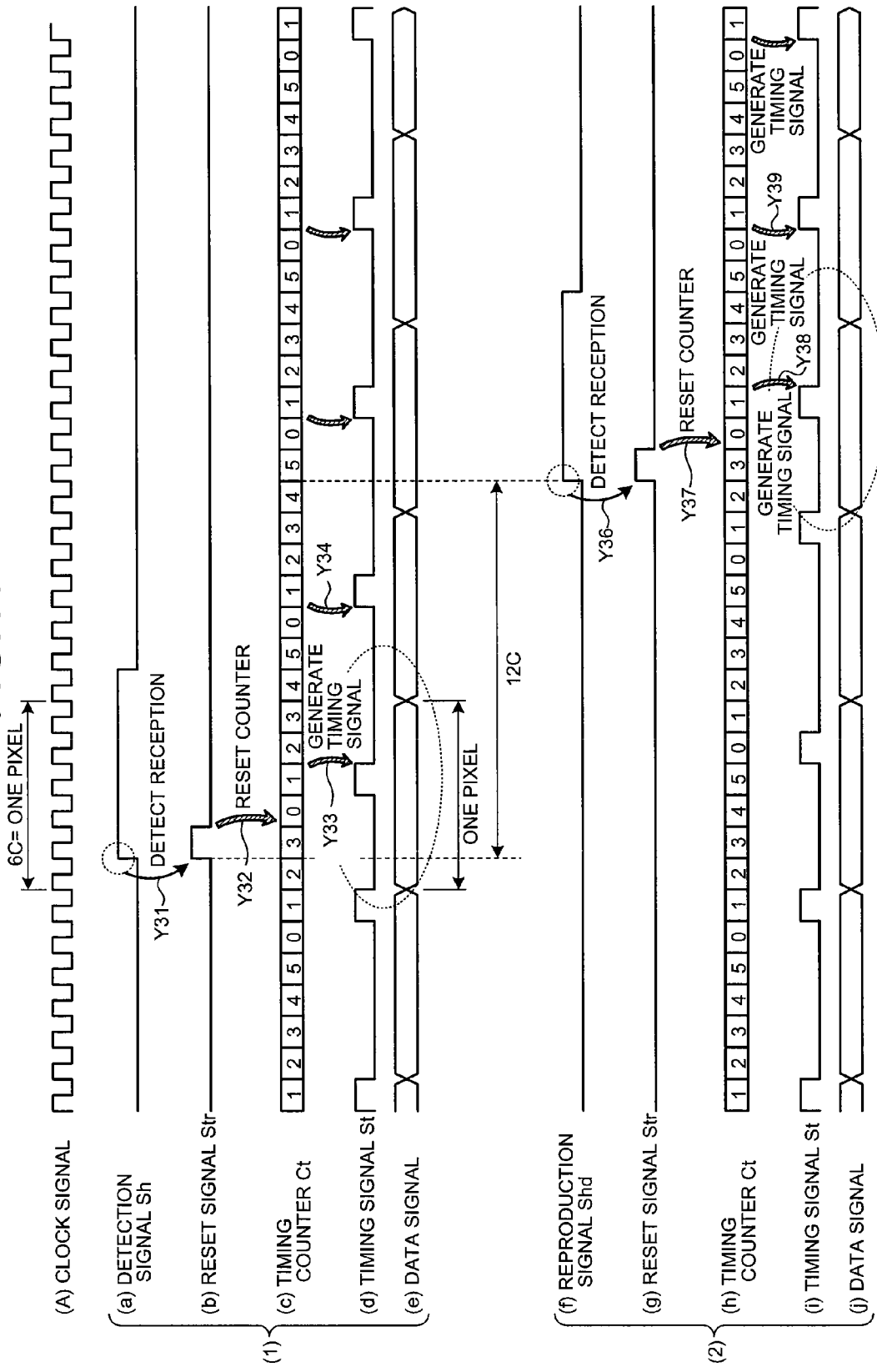
FIG. 11 is a timing chart for explaining a processing operation performed by a timing signal generator shown in FIG. 5.

A signal processing of the generation of the timing signal St by the timing signal generator 238 is explained next with reference to a timing chart shown in FIG. 11. FIG. 11(1) corresponds to a generation of the timing signal St using the detection signal Sh by the timing signal generator 238. A symbol (a) corresponds to the detection signal Sh, (b) corresponds to the reset signal Str that instructs a reset of the count value and a count starting to the timing counter Ct held by the timing signal generator 238. A symbol (c) corresponds to a count value of the timing counter Ct, (d) corresponds to the timing signal St generated by the timing signal generator 238, and (e) corresponds to a data signal in each scan line of the image signal S1 output from the converter 33. FIG. 11(2) corresponds to a generation of the timing signal St using the reproduction signal Shd by the timing signal generator 238. A symbol (f) corresponds to the reproduction signal Shd, (g) corresponds to the reset signal Str, (h) corresponds to a count value of the timing counter Ct, (i) corresponds to the timing signal St, and (j) corresponds to a data signal. In FIG. 11, each signal and each counter are processed based on the clock signal shown by (A). The timing counter Ct starts counting from a count value "0". When the count value proceeds to "5", the count value is automatically reset to "0", and the timing counter Ct progresses counting. As shown in the data signals (e) and (j) that show each pixel information out of the signal Sa input to the converter 33, one pixel has a signal width of 6C, and the timing counter Ct counts corresponding to a signal width per one pixel.

First, generation of the timing signal St using the detection signal Sh by the timing signal generator 238 is explained with reference to FIG. 11(1). In FIG. 11(a), when a reception of the detection signal Sh is detected, the timing signal generator 238 outputs the reset signal Str shown in (b) to the timing counter Ct, as shown by an arrowhead Y31. As a result, as shown by an arrowhead Y32, the count value of the timing counter Ct shown in (c) is reset to "0", and the timing counter Ct progresses the counting. The timing signal generator 238 generates the reset signal Str while the count value of the timing counter Ct is "1", as shown by an arrowhead Y33 and (d). In this case, as shown by an arrowhead Y34, the timing signal generator 238 generates the next reset signal Str, before the count value of the timing counter Ct next becomes "1", that is, by matching the next signal in the data signal. In this way, the timing signal generator 238 sequentially generates the timing signal St in each pixel unit of the data signal, by matching the count value "1" of the timing counter Ct. This reset signal Str is output to reset the timing counter Ct at substantially the center of the signal width per one pixel of a data signal. Substantially the center of the signal width per one pixel of a data signal corresponds to an information body showing luminance of a pixel. Therefore, the synchronization signal detector 34 generates the timing signal St at substantially the center of the signal width per one pixel of a data signal, and instructs the image processor 35 to perform processing. With this arrangement, the image processor 35 can securely acquire luminance information of a pixel.

Generation of the timing signal St using the reproduction signal Shd by the timing signal generator 238 is explained with reference to FIG. 11(2). Like the operation shown in FIG. 11(1), when a reception of the reproduction signal Shd is detected as shown by (f), the timing signal generator 238 outputs the reset signal Str as shown by an arrowhead Y36 and (g). As a result, the count value of the reset counter Ctr is reset as shown by an arrowhead Y37, and the timing signal generator 238 generates the timing signal St in each one pixel unit of a data signal, as shown by arrowheads Y38 and Y39 and (i).

The timing signal generator 238 converts the generated timing signal St to correspond to a signal format of the image signal S1 output from the converter 33, and outputs the converted signal to the image processor 35. For example, when the signal Sa input to the converter 33 is in a serial format, and when the converter 33 processes the signal Sa and outputs the image signal S1 in a parallel format, the timing signal generator 238 converts the generated timing signal St to correspond to a parallel format.

As shown in (a) and (f), the reproduction signal Shd is input to the timing signal generator 238 with a delay of 12C corresponding to two pixels, from the detection signal Sh. As a result, when the timing signal generator 238 generates the timing signal St by using the reproduction signal Shd, the timing signal generator 238 generates this timing signal St with a delay of two pixels from the timing of generating the timing signal St using the detection signal Sh. As a result, the synchronization controller 239 makes the timing signal generator 238 output the timing signal St to the image processor 35 by matching the timing of inputting the image signal S1 to the image processor 35. Therefore, the output timing of the timing signal St generated using the detection signal Sh needs to be changed from the output timing of the timing signal St generated using the reproduction signal Shd. In other words, as explained at step S218 and step S220 in FIG. 6, the timing signal generator 238 outputs the timing signal St based on the detection signal Sh, using the reference timing, and outputs the timing signal St based on the reproduction signal Shd, using the reproduction signal timing.

Figure 12:
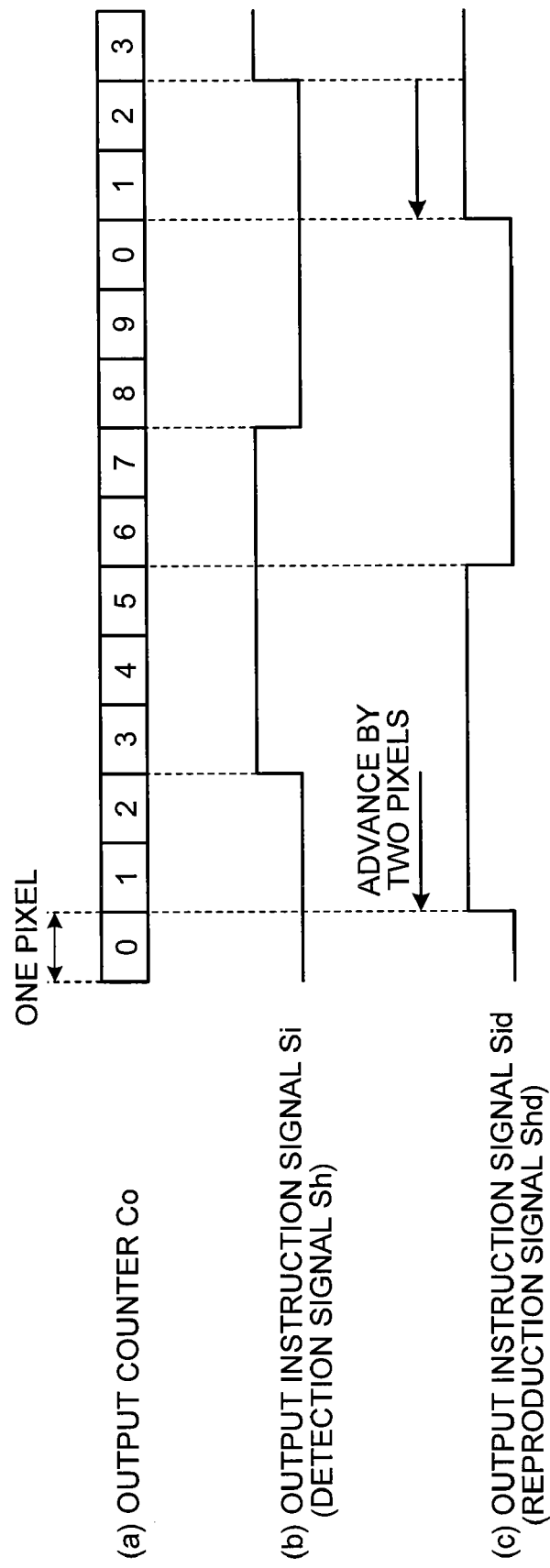
FIG. 12 is a timing chart for explaining the processing operation performed by the timing signal generator shown in FIG. 5.

The reference timing and the reproduction signal timing at which the timing signal St is output from the timing signal generator 238, respectively are explained with reference to FIG. 12. FIG. 12(a) shows a count value of an output counter Co held by the synchronization controller 239. This output counter Co starts counting based on a reception of the detection signal Sh or the reproduction signal Shd, and counts for each signal width corresponding to one pixel of the image signal S1 output from the converter 33. When the count value proceeds to "9", the output counter Co resets the count value to "0", and progresses the counting. A symbol (b) corresponds to an output instruction signal Si to the timing signal St generated based on the detection signal Sh, among output instruction signals output from the synchronization controller 239 to the timing signal generator 238. In other words, the output instruction signal Si corresponds to the reference timing. A symbol (c) corresponds to an output instruction signal Sid to the timing signal St generated based on the detection signal Shd. In other words, the output instruction signal Sid corresponds to the reproduction signal timing. The reference symbols (b) and (c) show the output of the timing signal St at a duty rate 50%.

As shown in FIG. 12(b), for the timing signal St based on the detection signal Sh, the synchronization controller 239 outputs the output instruction signal Si during a period from the count value "3" to the count value "7", and instructs the timing signal generator 238 to output the timing signal St. In this case, the timing signal generator 238 outputs the timing signal St to the image processor 35 during the period from the count value "3" to the count value "7", following the instruction of the output instruction signal Si. As explained above, the timing signal generator 238 outputs the timing signal St from the count value "3" of the output counter Co, using this reference timing.

On the other hand, as shown in FIG. 12(c), for the timing signal St based on the reproduction signal Shd, the synchronization controller 239 outputs the output instruction signal Sid during the count value "1" and the count value "5", by advancing two counts from the output instruction signal Si, and instructs the timing signal generator 238 to output the timing signal St. As explained above, the timing signal St generated based on the reproduction signal Shd is output at the timing that absorbs the delay in the input of the reproduction signal Shd. In other words, the period from when the reproduction signal Shd is input until when the timing signal St generated based on the reproduction signal Shd is output is decreased by the period corresponding to the generation period of the reproduction signal generated by the reproducing unit 237, that is, the period corresponding to two pixel components, as compared with the period from when the detection signal Sh is input until when the timing signal St generated based on the detection signal Sh is output.

As explained above, the synchronization controller 239 makes the timing signal generator 238 output the timing signal St to the image processor 35 at the timing corresponding to the input times of the detection signal Sh and the reproduction signal Shd to the timing signal generator 238, respectively. Therefore, the synchronization signal detector 34 can output the timing signal St using the detection signal Sh and the timing signal St using the reproduction signal Shd to the image processor 35, respectively, by matching the timing when the image signal S1 is input to the image processor 35, thereby accurately instructing the image processing timing of the image processor 35.

According to the receiving apparatus 3 of the first embodiment, when the horizontal synchronization signal detector 236 cannot detect a horizontal synchronization signal by a predetermined number or more, or when the horizontal synchronization signal detector 236 cannot continuously detect a horizontal synchronization signal by a predetermined number of times or more, or when the vertical synchronization signal detector 246 cannot continuously detect a vertical synchronization signal by a predetermined number of times or more, for the image signal of one frame, respectively, the image deletion controller 36a deletes the image corresponding to this frame as a defective image. Therefore, only accurate image information having no noise can be acquired. Further, because an image having a possibility of containing much external noise is deleted, image information can be stored at a high compression rate. When the horizontal synchronization signal detector 236 and the vertical synchronization signal detector 246 cannot detect a synchronization signal, the reproducing units 237 and 247 generate the reproduction signals Shd and Vhd, and the image processor 35 starts processing the image signal S1 based on the reproduction signals Shd and Vhd. Therefore, accurate image information having no noise can be acquired, even when the synchronization signal detector 34 cannot detect a certain number of synchronization signals.

(Second Embodiment)

Figure 13:
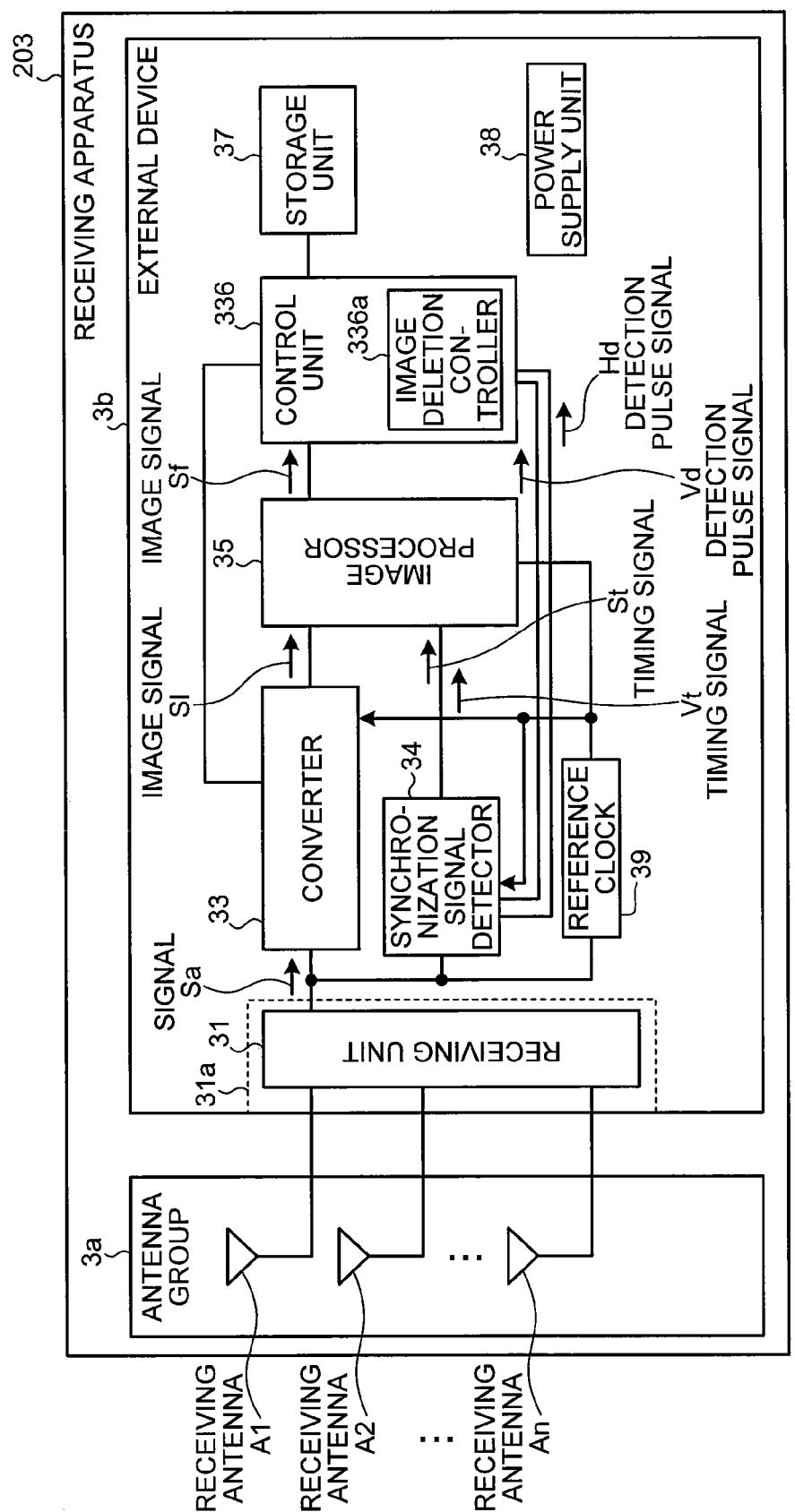
FIG. 13 is a schematic block diagram showing an entire configuration of a receiving apparatus according to a second embodiment of the present invention.

A second embodiment is explained next. FIG. 13 is a schematic block diagram showing an entire configuration of a receiving apparatus 203 according to the second embodiment. The receiving apparatus 203 shown in FIG. 13 is different from the receiving apparatus 3 shown in FIG. 2 in that an image deletion controller 336a has a configuration different from that of the image deletion controller 36a. Other configurations are the same as those of the receiving apparatus 3, and like constituent elements are denoted with like reference letters or numerals.

Figure 14:
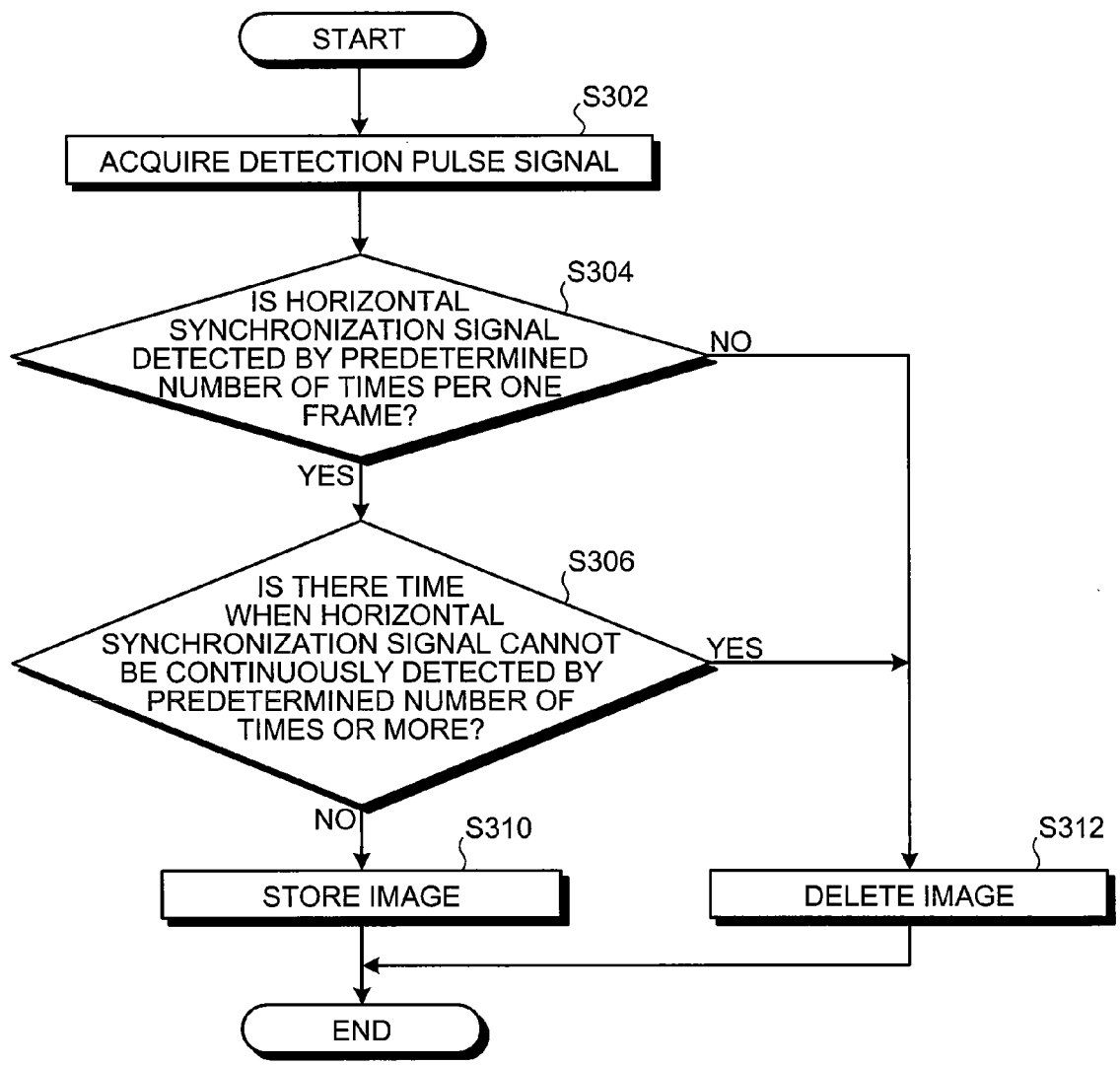
FIG. 14 is a flowchart for showing a process procedure of image deletion control performed by an image deletion controller shown in FIG. 13.

A process procedure of image deletion control performed by the image deletion controller 336a is explained below with reference to a flowchart shown in FIG. 14. First, the image deletion controller 336a acquires a detection pulse signal Hd of a horizontal synchronization signal (step S302). Thereafter, the image deletion controller 336a determines whether the horizontal synchronization signal detector 236 can detect a horizontal synchronization signal by a predetermined number or more per one frame, based on the detection pulse signal Hd of a horizontal synchronization signal (step S304). When it is determined that the horizontal synchronization signal detector 236 cannot detect a horizontal synchronization signal by a predetermined number or more per one frame (step S304: No), the image deletion controller 336a deletes the image of this frame as a defective image (step S312).

On the other hand, when it is determined that the horizontal synchronization signal detector 236 can detect a horizontal synchronization signal by a predetermined number or more per one frame (step S304: Yes), the image deletion controller 336a further determines whether the horizontal synchronization signal detector 236 has not been able to continuously detect a horizontal synchronization signal by a predetermined number of times or more in one frame, based on the detection pulse signal Hd of a horizontal synchronization signal (step S306). When the image deletion controller 336a determines that the horizontal synchronization signal detector 236 has not been able to continuously detect a horizontal synchronization signal by a predetermined number of times or more (step S306: Yes), the image deletion controller 336a deletes the image of this frame as a defective image (step S312).

On the other hand, when the image deletion controller 336a determines that the horizontal synchronization signal detector 236 has not been able to continuously detect a horizontal synchronization signal by a predetermined number of times or more (step S306: No), that is, when it is determined that the horizontal synchronization signal detector 236 can detect a horizontal synchronization signal by a predetermined number or more per one frame (step S304: Yes), and also when it is determined that the horizontal synchronization signal detector 236 has not been able to continuously detect a horizontal synchronization signal by a predetermined number of times or more (step S306: No), the image deletion controller 336a controls to store the image of this frame into the storage unit 37 (step S310), and ends the process. In the second embodiment, it is not determined whether the vertical synchronization signal detector 246 has not been able to continuously detect a vertical synchronization signal by a predetermined number of times or more. According to the receiving apparatus 3 of the second embodiment, an operation effect substantially similar to that of the receiving apparatus 3 according to the first embodiment can be acquired.

(Third Embodiment)

Figure 15:
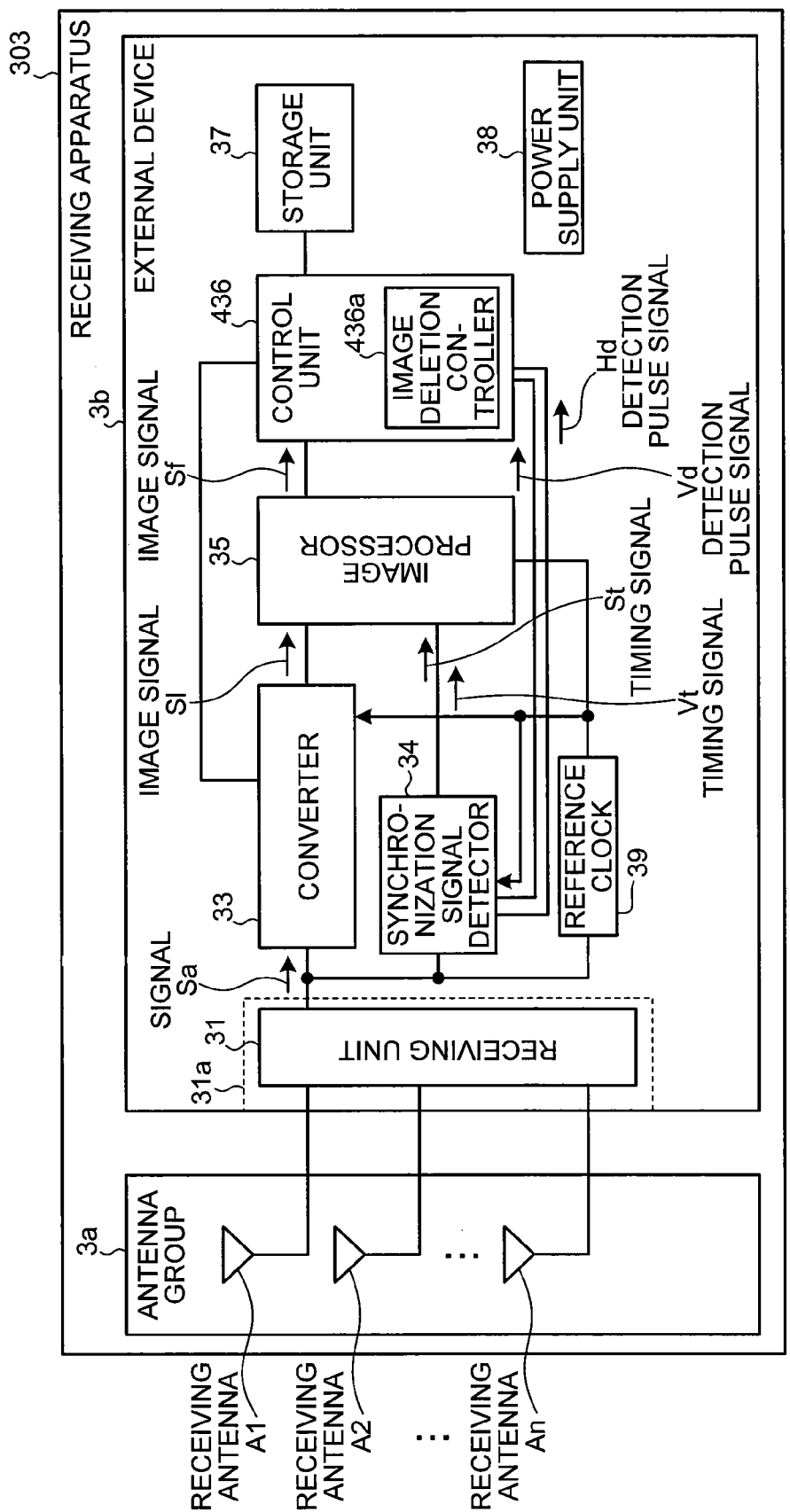
FIG. 15 is a schematic block diagram showing an entire configuration of a receiving apparatus according to a third embodiment of the present invention.

A third embodiment is explained next. FIG. 15 is a schematic block diagram showing an entire configuration of a receiving apparatus 303 according to the third embodiment. The receiving apparatus 303 shown in FIG. 15 is different from the receiving apparatus 3 shown in FIG. 2 in that an image deletion controller 436a has a configuration different from that of the image deletion controller 36a. Other configurations are the same as those of the receiving apparatus 3, and like constituent elements are denoted with like reference letters or numerals.

Figure 16:
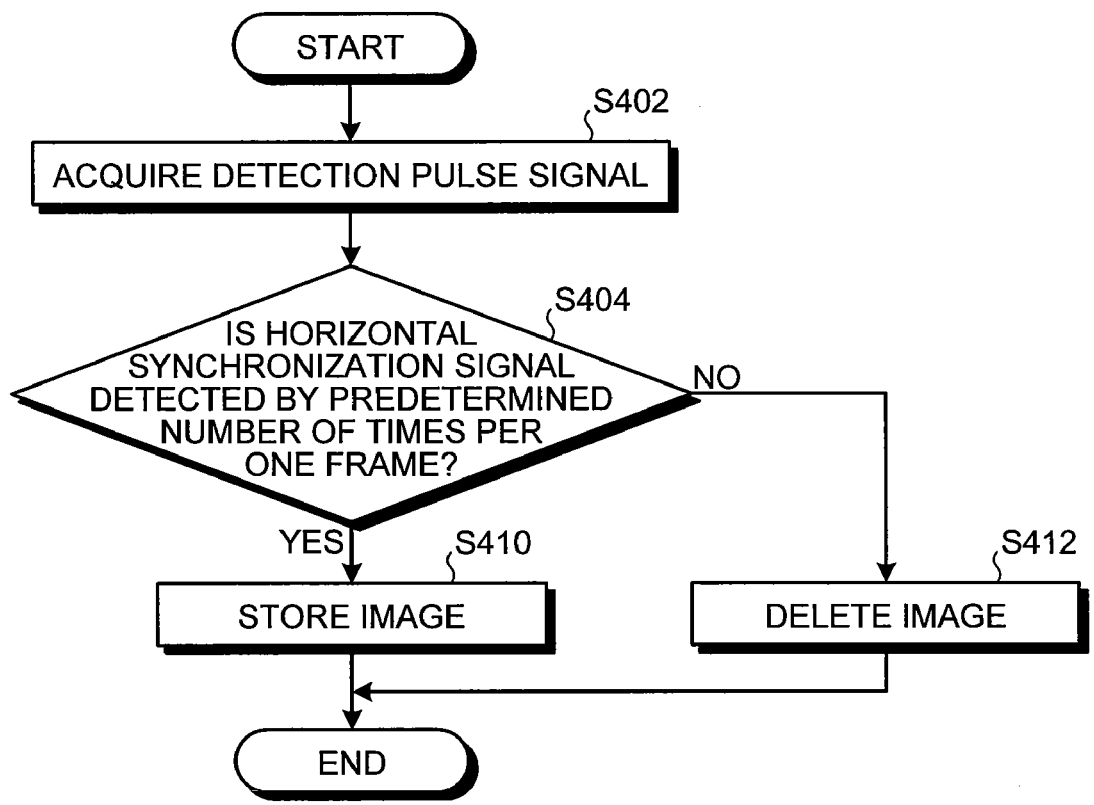
FIG. 16 is a flowchart for showing a process procedure of image deletion control performed by an image deletion controller shown in FIG. 15.

A process procedure of image deletion control performed by the image deletion controller 436a is explained below with reference to a flowchart shown in FIG. 16. First, the image deletion controller 436a acquires the detection pulse signal Hd of a horizontal synchronization signal (step S402). Thereafter, the image deletion controller 436a determines whether the horizontal synchronization signal detector 236 can detect a horizontal synchronization signal by a predetermined number or more per one frame, based on the detection pulse signal Hd of a horizontal synchronization signal (step S404). When it is determined that the horizontal synchronization signal detector 236 cannot detect a horizontal synchronization signal by a predetermined number or more per one frame (step S404: No), the image deletion controller 436*a* deletes the image of this frame as a defective image (step S412).

On the other hand, when it is determined that the horizontal synchronization signal detector 236 can detect a horizontal synchronization signal by a predetermined number or more per one frame (step S404: Yes), the image deletion controller 336*a* controls to store the image of this frame into the storage 37 (step S410). In the third embodiment, it is not determined whether the horizontal synchronization signal detector 236 has not been able to continuously detect a horizontal synchronization signal by a predetermined number of times or more. However, because it is determined whether the horizontal synchronization signal detector 236 can detect a horizontal synchronization signal by a predetermined number or more per one frame, accurate image information having no noise can be acquired, and the image information can be stored at a high compression rate.

(Fourth Embodiment)

Figure 17:
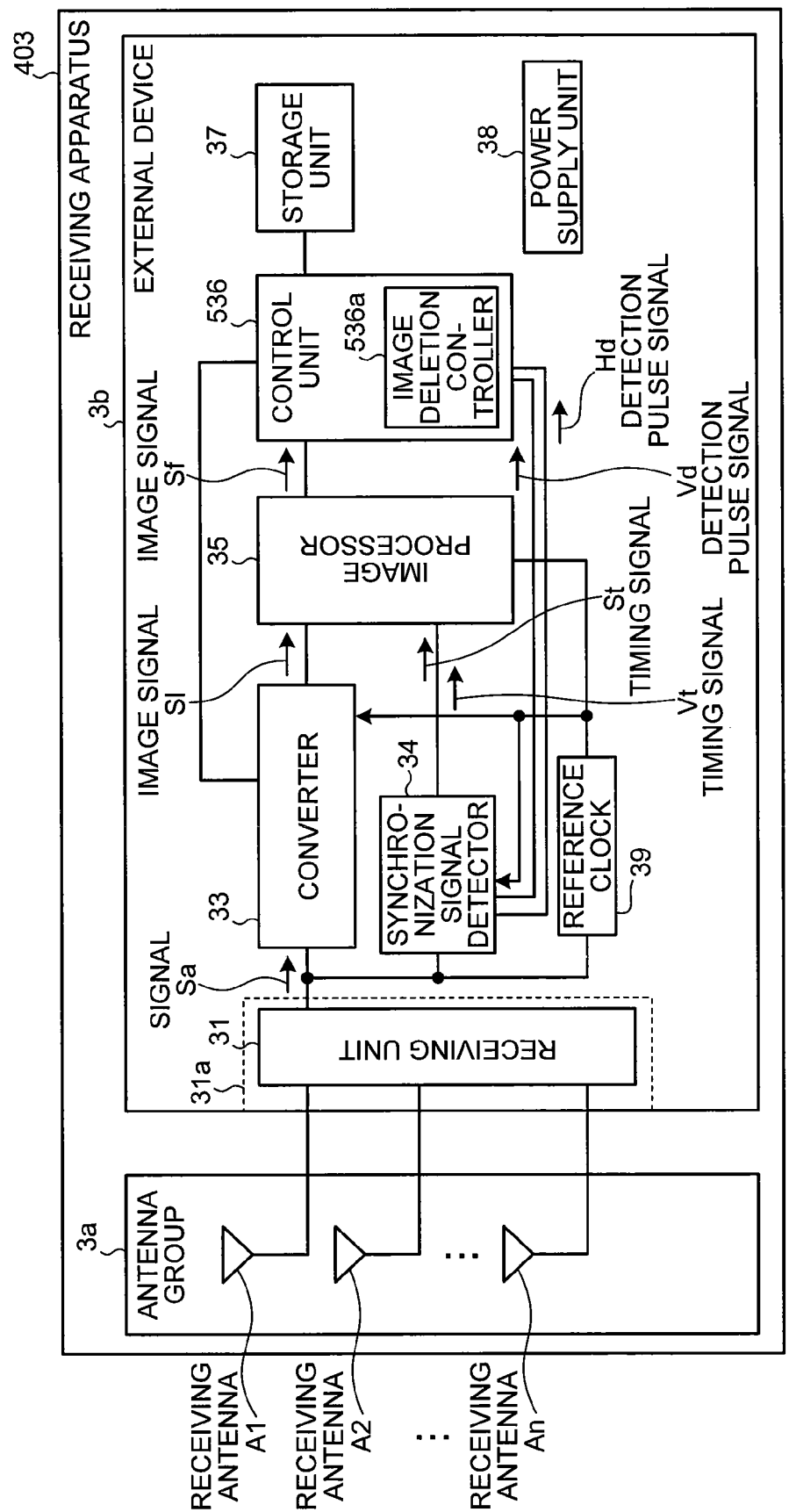
FIG. 17 is a schematic block diagram showing an entire configuration of a receiving apparatus according to a fourth embodiment of the present invention.

A fourth embodiment is explained next. FIG. 17 is a schematic block diagram showing an entire configuration of a receiving apparatus 403 according to a fourth embodiment. The receiving apparatus 403 shown in FIG. 17 is different from the receiving apparatus 3 shown in FIG. 2 in that an image deletion controller 536*a* has a configuration different from that of the image deletion controller 36*a*. Other configurations are the same as those of the receiving apparatus 3, and like constituent elements are denoted with like reference letters or numerals.

Figure 18:
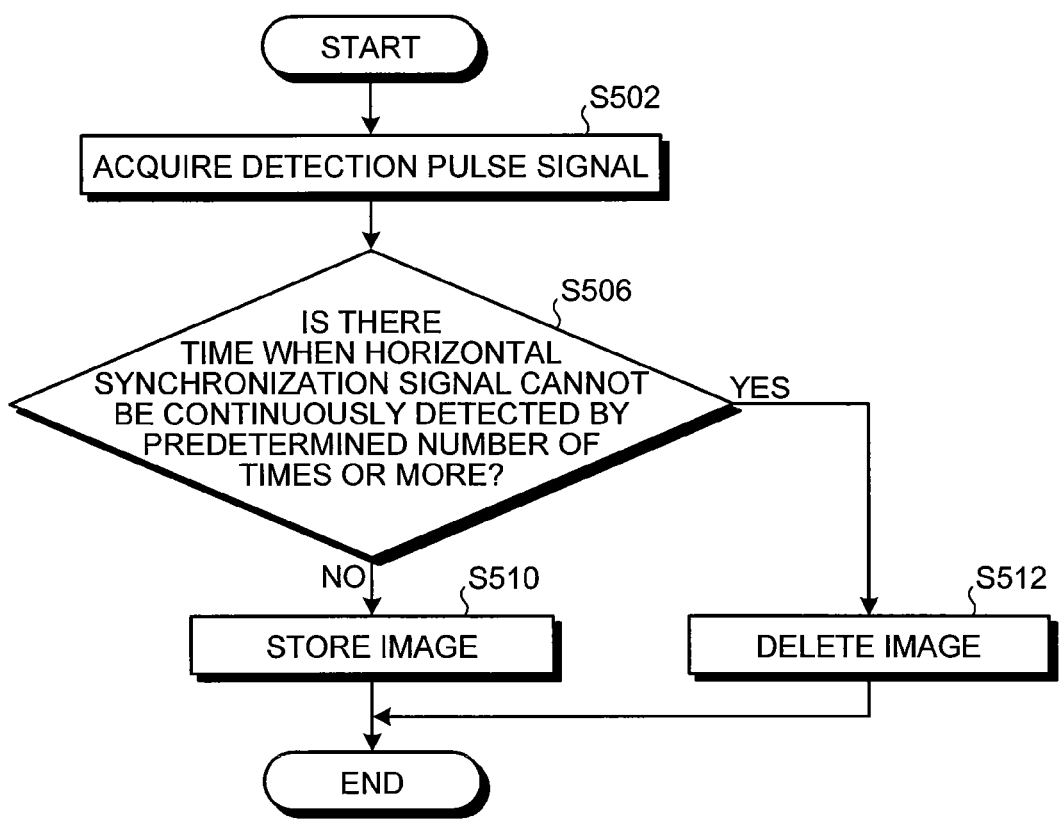
FIG. 18 is a flowchart for showing a process procedure of image deletion control performed by an image deletion controller shown in FIG. 17.

A process procedure of image deletion control performed by the image deletion controller 536*a* is explained below with reference to a flowchart shown in FIG. 18. First, the image deletion controller 536*a* acquires the detection pulse signal Hd of a horizontal synchronization signal (step S502). Thereafter, the image deletion controller 536*a* determines whether there is a time when the horizontal synchronization signal detector 236 cannot continuously detect a horizontal synchronization signal by a predetermined number of times or more in one frame, based on the detection pulse signal Hd of a horizontal synchronization signal (step S506). When it is determined that there is a time when the horizontal synchronization signal detector 236 cannot continuously detect a horizontal synchronization signal by a predetermined number of times or more (step S506: Yes), the image deletion controller 536*a* deletes the image of this frame as a defective image (step S512).

On the other hand, when it is determined that there is no time when the horizontal synchronization signal detector 236 cannot continuously detect a horizontal synchronization signal by a predetermined number of times or more (step S506: No), the image deletion controller 536*a* controls to store the image of this frame into the storage 37 (step S510). In the fourth embodiment, it is not determined whether the horizontal synchronization signal detector 236 has not been able to detect a horizontal synchronization signal by a predetermined number or more per one frame. However, because it is determined whether there is a time when the horizontal synchronization signal detector 236 cannot continuously detect a horizontal synchronization signal by a predetermined number of times or more in one frame, accurate image information having no noise can be acquired.

The receiving apparatus and the intra-subject information acquiring system according to the present invention are not limited to the above embodiments, and can be changed within a range of the idea of the present invention. For example, the image deletion controller 36*a* can determine only whether the vertical synchronization detector 246 cannot continuously detect a vertical synchronization signal by a predetermined number of times or more, and delete or store the image based on a result of this determination.

Industrial Applicability

As described above, the receiving apparatus and the intra-subject information acquiring system according to the present invention are useful for a receiving apparatus that processes a radio signal containing an information component transmitted from a transmitting apparatus, and for an intra-subject information acquiring system. Particularly, the receiving apparatus and the intra-subject information acquiring system according to the present invention are useful for a receiving apparatus that processes a radio signal containing an information component transmitted from a capsule endoscope as a transmitting apparatus, and for an intra-subject information acquiring system.

The invention claimed is:

1. A receiving apparatus comprising:
   a detector that detects a horizontal synchronization signal from an image signal of one frame having a plurality of line information components and the horizontal synchronization signal attached to each line information component;
   an image processor that performs an image generation process of each frame based on the horizontal synchronization signal detected by the detector;
   a controller that controls to delete an image of a current frame, when the detector does not detect a predetermined number or more horizontal synchronization signals within one frame; and
   a reproduction signal generator that generates a horizontal reproduction signal based on a horizontal synchronization signal detected earlier by the detector in such a manner that the horizontal reproduction signal corresponds to the horizontal synchronization signal, when the detector fails to detect the horizontal synchronization signal,
   wherein the image processor starts processing a line information component from which the detector has failed to detect the horizontal synchronization signal, based on the horizontal reproduction signal.

2. A receiving apparatus comprising:
   a detector that detects a horizontal synchronization signal from an image signal of one frame having a plurality of line information components and the horizontal synchronization signal attached to each line information component;
   an image processor that performs an image generation process of each frame based on the horizontal synchronization signal detected by the detector;
   a controller that controls to delete an image of a current frame, when the detector does not continuously detect a predetermined number or more horizontal synchronization signals within one frame; a reproduction signal generator that generates a horizontal reproduction signal based on a horizontal synchronization signal detected earlier by the detector in such a manner that the horizontal reproduction signal corresponds to the horizontal synchronization signal, when the detector fails to detect the horizontal synchronization signal,
   wherein the image processor starts processing a line information component from which the detector has failed to detect the horizontal synchronization signal, based on the horizontal reproduction signal.

3. A receiving apparatus comprising:
a detector that detects a vertical synchronization signal from an image signal of one frame having a plurality of line information components and the vertical synchronization signal attached to plural line information components;
an image processor that performs an image generation process of each frame based on the vertical synchronization signal detected by the detector;
a controller that controls to delete an image of a current frame, when the detector does not continuously detect a predetermined number or more vertical synchronization signals;
a vertical reproduction signal generator that generates a vertical reproduction signal based on a vertical synchronization signal detected earlier by the detector in such a manner that the vertical reproduction signal corresponds to the vertical synchronization signal, when the detector fails to detect the vertical synchronization signal,
wherein the image processor starts processing a frame from which the detector has failed to detect the vertical synchronization signal, based on the vertical reproduction signal.

4. A receiving apparatus comprising:
a detector that detects a horizontal synchronization signal and a vertical synchronization signal from an image signal of one frame having a plurality of line information components and the horizontal synchronization signal attached to each line information component;
an image processor that performs an image generation process of each frame based on the horizontal synchronization signal and the vertical synchronization signal detected by the detector;
a controller that controls to delete an image of a current frame, when the detector does not continuously detect a first predetermined number or more horizontal synchronization signals within one frame, or when the detector does not detect a second predetermined number or more horizontal synchronization signals within one frame, or when the detector does not continuously detect a third predetermined number or more vertical synchronization signals; a reproduction signal generator that generates a horizontal reproduction signal based on a horizontal synchronization signal detected earlier by the detector in such a manner that the horizontal reproduction signal corresponds to the horizontal synchronization signal, when the detector fails to detect the horizontal synchronization signal; and
a vertical reproduction signal generator that generates a vertical reproduction signal based on a vertical synchronization signal detected earlier by the detector in such a manner that the vertical reproduction signal corresponds to the vertical synchronization signal, when the detector has failed to detect the vertical synchronization signal,
wherein the image processor starts processing a line information component from which the detector has failed to detect the horizontal synchronization signal, based on the horizontal reproduction signal, and the image processor starts processing a frame from which the detector fails to detect the vertical synchronization signal, based on the vertical reproduction signal.

5. The receiving apparatus according to claim 1, comprising a storage unit that stores an image of each frame generated by the image processor.

6. The receiving apparatus according to claim 1, wherein when the detector does not detect the horizontal synchronization signal for a predetermined period after detecting one horizontal synchronization signal, the reproduction signal generator generates the horizontal reproduction signal.

7. The receiving apparatus according to claim 1, wherein when the detector fails to continuously detect the horizontal synchronization signal two or more times, the controller controls to delete the image of the current frame.

8. The receiving apparatus according to claim 2, comprising a storage unit that stores an image of each frame generated by the image processor.

9. The receiving apparatus according to claim 3, comprising a storage unit that stores an image of each frame generated by the image processor.

10. The receiving apparatus according to claim 4, comprising a storage unit that stores an image of each frame generated by the image processor.

11. The receiving apparatus according to claim 1, comprising a storage unit that stores an image of each frame generated by the image processor, wherein
when the detector detects the predetermined number or more horizontal synchronization signals within one frame, the controller causes the storage unit to store the image of the current frame.

12. The receiving apparatus according to claim 1, comprising a storage unit that stores an image of each frame generated by the image processor, wherein
when the detector continuously detects the predetermined number or more horizontal synchronization signals within one frame, the controller causes the storage unit to store the image of the current frame.

13. The receiving apparatus according to claim 2, wherein when the detector does not detect the horizontal synchronization signal for a predetermined period after detecting one horizontal synchronization signal, the reproduction signal generator generates the horizontal reproduction signal.

14. The receiving apparatus according to claim 4, wherein when the detector does not detect the horizontal synchronization signal for a predetermined period after detecting one horizontal synchronization signal, the reproduction signal generator generates the horizontal reproduction signal.

15. The receiving apparatus according to claim 2, wherein when the detector fails to continuously detect the horizontal synchronization signal two or more times, the controller controls to delete the image of the current frame.

16. The receiving apparatus according to claim 4, wherein when the detector fails to continuously detect the horizontal synchronization signal two or more times, the controller controls to delete the image of the current frame.

* * * * *